(12) United States Patent
Consigny et al.

(10) Patent No.: US 8,708,948 B2
(45) Date of Patent: Apr. 29, 2014

(54) INTRACORONARY DEVICE AND METHOD OF USE THEREOF

(75) Inventors: Paul Consigny, San Jose, CA (US);
Gabriel Asongwe, San Jose, CA (US);
Mary Beth Michaels, Sunnyvale, CA (US); Gene Michal, San Francisco, CA (US); Evgenia Mandrusov, Santa Clara, CA (US); Jeong Lee, Diamond Bar, CA (US); Florian N. Ludwig, Luzern (CH);
John Eric Henckel, Houston, TX (US);
Joseph J. Sciacca, Houston, TX (US);
Ken Bueche, Friendswood, TX (US);
Richard Todd Thornton, League City, TX (US); Fidel Albert Urrabazo, San Antonio, TX (US); Daniel Wiegand, Houston, TX (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/401,803

(22) Filed: Feb. 21, 2012

(65) Prior Publication Data

US 2012/0148668 A1 Jun. 14, 2012

Related U.S. Application Data

(62) Division of application No. 11/170,750, filed on Jun. 29, 2005, now abandoned.

(51) Int. Cl.
*A61K 35/12* (2006.01)
*A61K 9/127* (2006.01)
*A61M 37/00* (2006.01)
*A61P 41/00* (2006.01)

(52) U.S. Cl.
USPC .................. 604/24; 424/450; 424/93.7

(58) Field of Classification Search
USPC .......... 604/24, 23, 82–86, 522, 43, 45, 26–27, 604/288.04, 507, 508, 509; 424/450, 93.7
See application file for complete search history.

(56) References Cited

U.S. PATENT DOCUMENTS

| 3,512,517 | A | * | 5/1970 | Hall et al. | 600/347 |
|---|---|---|---|---|---|
| 4,069,814 | A | * | 1/1978 | Clemens | 600/581 |
| 4,385,631 | A | * | 5/1983 | Uthmann | 604/284 |
| 4,553,957 | A | * | 11/1985 | Williams et al. | 604/43 |
| 4,904,238 | A | * | 2/1990 | Williams | 604/43 |
| 4,979,942 | A | * | 12/1990 | Wolf et al. | 604/83 |

(Continued)

FOREIGN PATENT DOCUMENTS

| WO | WO 92/08796 | 5/1992 |
|---|---|---|
| WO | WO 94/28143 | 12/1994 |

(Continued)

OTHER PUBLICATIONS

International Search Report for PCT/US2006/021964, filed Jun. 6, 2006, mailed May 22, 2007, 19 pgs.

(Continued)

*Primary Examiner* — Emily Schmidt
*Assistant Examiner* — Michael J Anderson
(74) *Attorney, Agent, or Firm* — Squire Sanders (US) LLP

(57) ABSTRACT

Engraftment of therapeutic cells and agents to a target site in an organism is enhanced by mechanical, chemical and biological methods and systems.

18 Claims, 6 Drawing Sheets

(56) References Cited

U.S. PATENT DOCUMENTS

| | | | |
|---|---|---|---|
| 5,009,634 A * | 4/1991 | Feldman et al. | 604/27 |
| 5,084,011 A * | 1/1992 | Grady | 604/24 |
| 5,103,821 A | 4/1992 | King | |
| 5,130,141 A | 7/1992 | Law et al. | |
| 5,342,298 A | 8/1994 | Michaels et al. | |
| 5,441,482 A * | 8/1995 | Clague et al. | 604/35 |
| 5,486,359 A | 1/1996 | Caplan et al. | |
| 5,543,318 A | 8/1996 | Smith et al. | |
| 5,569,180 A * | 10/1996 | Spears | 604/24 |
| 5,580,779 A | 12/1996 | Smith et al. | |
| 5,718,678 A * | 2/1998 | Fleming, III | 604/43 |
| 5,811,094 A | 9/1998 | Caplan et al. | |
| 5,831,012 A | 11/1998 | Nilsson et al. | |
| 6,090,622 A | 7/2000 | Gearhart et al. | |
| 6,245,566 B1 | 6/2001 | Gearhart et al. | |
| 6,534,628 B1 | 3/2003 | Nilsson et al. | |
| 6,663,596 B2 * | 12/2003 | Griego et al. | 604/164.02 |
| 6,676,627 B1 * | 1/2004 | Bonnette et al. | 604/22 |
| 6,740,734 B1 | 5/2004 | Nilsson et al. | |
| 6,758,828 B2 * | 7/2004 | Hammer et al. | 604/43 |
| 2002/0099026 A1 | 7/2002 | Goodman et al. | |
| 2002/0110910 A1 | 8/2002 | Gwathmey et al. | |
| 2004/0136967 A1 | 7/2004 | Weiss et al. | |
| 2005/0008624 A1 | 1/2005 | Peled et al. | |
| 2005/0145258 A1 * | 7/2005 | Dong | 128/898 |
| 2005/0147692 A1 * | 7/2005 | Roth | 424/600 |
| 2005/0245896 A1 * | 11/2005 | Kucharczyk et al. | 604/522 |
| 2007/0003528 A1 * | 1/2007 | Consigny et al. | 424/93.7 |
| 2008/0319377 A1 * | 12/2008 | Keenan | 604/24 |
| 2012/0148668 A1 * | 6/2012 | Consigny et al. | 424/450 |

FOREIGN PATENT DOCUMENTS

| | | |
|---|---|---|
| WO | WO 95/28494 | 10/1995 |
| WO | WO 95/34647 | 12/1995 |
| WO | WO 96/00295 | 1/1996 |
| WO | WO 2004/050180 | 6/2004 |

OTHER PUBLICATIONS

Figueroa et al, Hypertension, vol. 37, pp. 110-120 (2001).
Gazitt, Journal of Hematotherapy and Stem Cell Research, vol. 10, pp. 229-236 (2001).
Jeng-Jiann Chiu et al., "Shear Stress Increases ICAM-1 and Decreases VCAM-1 and E-selectin Expressions Induced by Tumor Necrosis Factor-α in Endothelial Cells", Arterioscler Thromb. Vasc. Biol., pp. 74-79 (2004).
Kimiko Yamamoto et al., "Proliferation, differentiation, and tube formation by endothelial progenitor cells in response to shear stress", J. Appl. Physiol. 95, pp. 2081-2088 (2003).
Peled et al, Journal of Clinical Investigations, vol. 104, pp. 1199-1211 (1999).
Rood et al, Experimental Hematology, vol. 27, pp. 1306-1314 (1999).
Williams et al, Nature, vol. 352, pp. 438-441(1991).
Ganguli et al., "Distinct NF-κB Regulation by Shear Stress Through Ras-Depenent IκBα Oscillations", Circ. Res. 96, pp. 626-634 (2005).
Heeschen et al., "Profoundly Reduced Neovascularization Capacity of Bone Marrow Mononuclear Cells Derived From Patients with Chronic Ischemic Heart Disease", Circulation 109, pp. 1615-1622 (2004).
Ng et al., "Adhesion of flowing monocytes to hypoxia-reoxygenation-exposed endothelial cells: role of Rac1, ROS, and VCAM-1", Am. J. Physiol. Cell Physiol. 283, pp. C93-C102 (2002).
Ohga et al., "The relationship between adhesion molecules and hypoxia", Nippon Rinsho, Japanese. J. of clinical m. vol. 58, No. 8, pp. 1587-1591 (2000). English Abstract.

* cited by examiner

FIG. 1B  FIG. 1C

- MOLECULE T PRESENT ON SURFACE OF THERAPEUTIC CELLS
- ◆ MOLECULE E PRESENT ON ENDOTHELIAL CELLS OF TARGET VASCULATURE
- ⊃⊂ LINKER MOLECULE COMPRISING ANTI-E AND ANTI-T

- MOLECULE T PRESENT ON SURFACE OF THERAPEUTIC CELLS
- MOLECULE E PRESENT ON ENDOTHELIAL CELLS OF TARGET VASCULATURE
- ⊃⊂ LINKER MOLECULE COMPRISING ANTI-E AND ANTI-T

- MOLECULE T PRESENT ON SURFACE OF THERAPEUTIC CELLS
- ◆ MOLECULE E PRESENT ON ENDOTHELIAL CELLS OF TARGET VASCULATURE
- NHS⋏ LINKER MOLECULE COMPRISING NHS AND ANTI-T

INTRACORONARY DEVICE AND METHOD OF USE THEREOF

This application is a divisional of U.S. application Ser. No. 11/170,750, filed on Jun. 29, 2005, the content of which is fully incorporated herein by reference in its entirety.

TECHNICAL FIELD

This document relates generally to delivery of therapeutic cells to a target site of a mammal and in particular, to a method and apparatus for enhancing engraftment at the target site.

BACKGROUND OF THE INVENTION

Damaged tissue, such as a lesion in a vessel, can be treated with therapeutic cells. For example, therapeutic cells can be injected into the vasculature to treat a lesion in the vessel. Some therapeutic cells will attach to the target site and provide treatment to the damaged tissue. However, depending on factors such as the dimensions of the target site, some of the therapeutic cells will flow past the lesion site without attaching to the site. Those therapeutic cells that fail to attach provide no benefit. Moreover, it has been reported that autologous bone marrow cells isolated from patients with chronic heart failure have "significantly reduced migratory and colony forming activity in vitro and a reduced neovascularization capacity in vivo" compared to cells from healthy controls (Circulation, 2004; 109: 1615-1622). The inability of such cells to migrate may lead to limited engraftment and colony forming activity may contribute to "limited therapeutic potential."

What is needed are methods and systems for improving the engraftment of therapeutic cells at a target site or region, e.g., a region of damaged tissue.

SUMMARY OF THE INVENTION

Various embodiments of the present subject matter provide enhanced migratory function, enhanced adhesion probability, increased residence time (for example longer residence time of the therapeutic cell in the coronary arteries), increased engraftment and increased likelihood of therapeutic potential. The methods and system disclosed herein include adding agents or secondary processing aimed at improving delivery and engraftment of delivered cells.

The efficiency of cell delivery and engraftment depends on factors including the infusion regimen, local milieu and the state of the cell.

For example, the infusion regimen includes such considerations as the shear rate and the cell residency time. In addition, the local milieu includes considerations such as the homing gradient, the presence of endothelial cells adhesion molecules, presence of bone marrow adhesion molecules and improved vessel permeability. Furthermore, the state of the cell is a function of cell viability, concentration and presence of adhesion molecules.

The invention comprises a method of enhancing engraftment of therapeutic cells at a target site in a mammal comprising conditioning the cells to provide cells having an altered number of adhesion molecules as compared to corresponding cells not subjected to the conditioning, wherein the conditioning increases the probability of engraftment of the cell at the target site; and delivering a composition comprising the conditioned therapeutic cells to the target site using a intercoronary delivery device.

The therapeutic cells of the present invention may comprise pluripotent, totipotent cells, autologous cells, non-autologous cells, or xenogenic cells. The methods of the present invention comprise conditioning the cells via biological conditioning, chemical conditioning, mechanical conditioning, or any combination thereof.

The methods of the invention comprise biological conditioning which comprises contacting the cell with at least one chemokine, cytokine, growth factor, or exogenous agent. The methods of the invention comparison biological conditioning which comprises subjecting the cells to periods of hypoxia.

The methods of the present invention further comprise conditioning cells associated with the target site to provide target cells having an altered number of adhesion molecules as compared to corresponding target cells not subjected to the conditioning, wherein the conditioning increases the probability of engraftment of the therapeutic cells at the target site.

The present invention provides a method of enhancing engraftment of a therapeutic cell at a target site in a mammal comprising delivering a composition comprising the therapeutic cell and one or more engraftment enhancing agents, wherein the composition is delivered to the target site using an intercoronary delivery device.

The present invention provides a method of enhancing engraftment of a therapeutic cell at a target site in a mammal comprising delivering a composition comprising the therapeutic cell and one or more engraftment enhancing agents, wherein the composition is delivered to the target site using an implantable delivery device, and wherein the one or more engraftment enhancing agents is biocompatible and provides transient, localized ischemia at the target site.

The present invention further provides a method of enhancing engraftment of a therapeutic cell at a target site in a mammal comprising delivering a composition comprising the therapeutic cell and one or more engraftment enhancing agents, wherein the composition is delivered to the target site using an implantable delivery device, and wherein the one or more engraftment enhancing agents is biodegradable and provides transient, localized ischemia at the target site.

The present invention also provides a method of enhancing engraftment of a therapeutic cell at a target site in a mammal comprising subjecting the therapeutic cell to in vitro conditioning, wherein the conditioning increases the probability of engraftment of the therapeutic cell at the target site; and delivering a composition comprising the conditioned therapeutic cell, wherein the composition is delivered to the target site using an implantable delivery device.

The present invention provides a catheter comprising a catheter body having a dual lumen, a mixing chamber at a terminus of the catheter body, the mixing chamber having an outlet, a porous material coupled to a first lumen to generate bubbles within the mixing chamber, a discharge port coupled to the second lumen to introduce a cell into the mixing chamber, and a bypass port to admit blood into the mixing chamber.

The present invention also provides a method comprising inducing ischemia at a target site for a transitory period of time, delivering a therapeutic cell and a viscous agent to the target site, the viscous agent selected to increase a viscosity of the therapeutic cell, and restoring normal blood flow to the target site.

The present invention provides a method of delivering a therapeutic cell to a target site in a mammal comprising introducing a solution including the therapeutic cell and an agent, wherein the agent is tailored to enhance engraftment of the therapeutic cell to the target site, and wherein the solution is introduced using an implantable catheter.

Also provided by the present invention is a method comprising modifying a target cell to upregulate an adhesion molecule counter-receptor, subjecting a therapeutic cell to mechanical conditioning so as to provide an increased number of adhesion molecules on the cell surface as compared to a non-conditioned cell, and delivering the therapeutic cell to the site of the target cell.

The present invention provides a method comprising combining a magnetic particle and a therapeutic cell, applying a static magnetic field to a target site of a mammal, the static magnetic field having a gradient oriented in a direction normal to a vessel wall at the target site, and introducing the therapeutic cell.

The present invention further provides a method of enhancing engraftment of therapeutic cells at a target site in a mammal comprising contacting the therapeutic cells with a biological linker, wherein at the linker is attached to the cell membrane of a therapeutic cell, and wherein at least one functionality of the linker molecule has affinity to the surface of the therapeutic cell, and wherein at least one other functionality of the linker has affinity to the surface of the lumen surface of the target area vasculature.

BRIEF DESCRIPTION OF THE DRAWINGS

In the drawings, like numerals describe similar components throughout the several views. Like numerals having different letter suffixes represent different instances of the components.

FIGS. 1A, 1B and 1C illustrate views of a shear module.

DETAILED DESCRIPTION

Figure 1A:
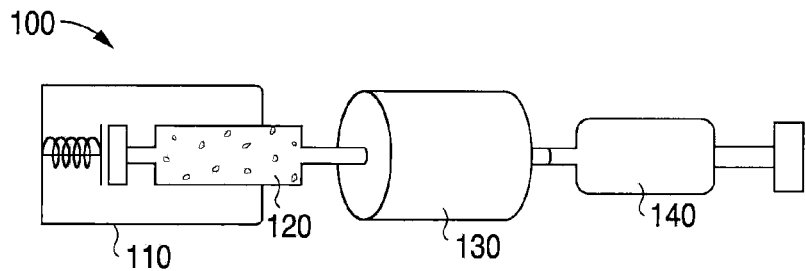

Reference will now be made in detail to certain claims of the invention, examples of which are illustrated in the accompanying text and examples. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

I. Definitions

An "engraftment enhancing agent" is defined herein as an agent or process of cellular manipulation that promotes, improves or enhances cellular engraftment of a therapeutic cell at a target site, for example, an agent that enhances the incorporation, i.e., adherence and/or transmigration, of a therapeutic cell in an area of infarcted myocardium. A process of cellular manipulation that enhances the incorporation of a therapeutic cell in a target site includes, for example, subjecting the therapeutic cell to conditioning, e.g., mechanical conditioning such as shear.

A "therapeutic cell" is appropriate cellular material introduced into and/or in the vicinity of damaged tissue. For example, a "therapeutic cell" includes, but is not limited to, a pluripotent or totipotent cell, e.g., a cell having broad developmental potential and "plasticity," for example, an "adult" stem cell, i.e., a post-natal stem cell, for example, a multipotent adult progenitor cell, or a cell derived from the bone marrow such as a hematopoietic stem cell (HSC), a hematopoietic progenitor cell, a non-hematopoietic mesenchymal stem cell (MSC), or a stromal cell; an embryonic stem cell, a cell from cord blood, an isolated $CD34^+$ cell, fetal cardiomyocytes, skeletal myoblasts, endothelial progenitor cells. By "therapeutic cell" is also meant skeletal muscle derived cells, for instance, skeletal muscle cells and skeletal myoblasts; cardiac derived cells, myocytes, e.g., ventricular myocytes, atrial myocytes, SA nodal myocytes, AV nodal myocytes, smooth muscle cells and fibroblasts. In one embodiment, the therapeutic cells are recombinant cells, such as recombinant $CD34^+$ cells. In another embodiment, the therapeutic cells are capillary endothelium. In yet another embodiment, the therapeutic cells are autologous cells including xenologous cells, however, non-autologous cells may be employed.

By "target cell" is meant a cell located at or in the vicinity of a "target site" in a subject to which a therapeutic cell is directed. A "target site" can be an area or region of vascular damage, disease or injury, or an area proximal to a region of vascular damage, disease, or injury. For example, a "target cell" can be an endothelial cell present on the lumen wall of a patient having myocardial injury or damage, such as in a patient having experienced myocardial infarction. A "target site" also includes vasculature, such as arterial and/or venous other than cardiac and/or coronary. In one example, a "target cell" is an endothelial cell residing in the vasculature of the target site.

By "myocardium" is meant the muscular portion of the heart. The myocardium includes three major types of muscle fibers: atrial muscle fibers, ventricular muscle fibers, and specialized excitatory and conductive muscle fibers.

"Ischemia" is a condition where oxygen demand of the tissue is not met due to localized reduction in blood flow caused by narrowing or occlusion of one or more vessels. "Occlusion" is the total or partial obstruction of blood flow through a vessel. By "transient, localized ischemia" is meant a temporary state of ischemia in a confined area of tissue caused by temporary total or partial obstruction of blood flow through a vessel. For example, "transient, localized ischemia" refers to a temporary decrease in blood flow below that needed to maintain adequate tissue oxygenation, also known as a supply demand imbalance or a demand that exceeds supply.

By "homing" or "homing process" is meant the migration of cells, e.g., therapeutic cells such as stem cells, and attachment to a target site, i.e., a site of injury or ischemia. Once attached, an environment is provided that is favorable to the growth and differentiation of cardiomyocytes because of increased vascular permeability, cytokine release, and adhesion protein expression. The expression of adhesion molecules, such as vascular endothelial growth factor (VEGF) and stromal cell-derived factor-1 (SDF-1), is up-regulated in hypoxic tissue.

As used herein, the phrase "adhesion molecules" refers to, for example, ligands and receptors that play a role in intercellular adhesion, such as the initiation of contact (tethering) between a therapeutic cell, e.g., a stem cell, and a target cell, e.g., an endothelial cell. For example, an endothelial cell present at the site of vascular injury expresses a receptor for a ligand expressed on a stem cell. Exemplary "adhesion molecules" that may be present on a therapeutic cell include, but are not limited to, CD44, P-selectin glycoprotein ligand-1 (PSGL-1; CD 162), hematopoietic cell E-/L-selectin ligand (HCELL), E-selectin ligand-1, Very Late Antigen-4 (VLA-4; CD49d), Leukocyte Function Associated Antigen-1 (LFA-1), an integrin, such as an $\alpha 4$ integrin or a $\beta 2$ integrin, CD31, VE-Cadherin (CD144), PECAM (CD31), vascular cell adhesion molecule-1 (VCAM-1), intercellular adhesion molecule (ICAM)-1, a selectin such as P-Selectin (CD62P), E-Selectin (CD62E), L-selectin, $\alpha 4\beta 7$, Mac-1, and cutaneous lymphocyte antigen. While not involved directed in inter-cellular adhesion per se, the phrase "adhesion molecules" also includes receptors that are present on either therapeutic cells or target cells, e.g., CD34, CD133, VEGF receptor 1 (flt-1/flk-2), VEGF receptor 2 (flk-1/KDR), and CXCR4, that can be utilized to manipulate the adhesion of a therapeutic cell to a target cell. For example, as discussed herein, bi-functional antibodies that specifically bind to CD133 may be utilized to modify the surface of a target cell.

To migrate to tissue(s), a therapeutic cell must first adhere to the target site with sufficient strength to overcome the shear forces of blood flow in a process known as "rolling." Once tethered, the therapeutic cell "rolls" via binding to its corresponding endothelial adhesion molecule.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, viral vectors (such as adenoviruses, adeno-associated viruses (AAV), lentiviruses, herpesvirus and retroviruses), liposomes and other lipid-containing complexes, and other macromolecular complexes (such as polycations, e.g., cationic polymers) capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA*, 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based, lipid-based or polymer-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene that is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector, such as via a recombinant AAV.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. There may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," or "sequence" that "encodes" a particular protein is a nucleic acid molecule that is transcribed and optionally also translated into a gene product, i.e., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer element" is meant a nucleic acid sequence that, when positioned proximate to a promoter, confers increased transcription activity relative to the transcription activity resulting from the promoter in the absence of the enhancer domain.

By "cardiac-specific enhancer element" is meant an element, which, when operably linked to a promoter, directs gene expression in a cardiac cell and does not direct gene expression in all tissues or all cell types. Cardiac-specific enhancers of the present subject matter may be naturally occurring or non-naturally occurring. One skilled in the art will recognize that the synthesis of non-naturally occurring enhancers can be performed using standard oligonucleotide synthesis techniques.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide or polypeptide refers to a nucleic acid sequence, peptide or polypeptide that is identified and separated from at least one contaminant nucleic acid, polypeptide or other biological component with which it is ordinarily associated in its natural source. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide," "polypeptide" and protein" are used interchangeably herein unless otherwise distinguished.

An "antibody" is a protein of the immune system that recognizes antigens and thereby triggers an immune response. By "antibody fragment" is meant a portion or part of an antibody having an antigen-binding domain.

Specific Embodiments of the Invention

In one specific embodiment, the present invention provides a method of enhancing engraftment of therapeutic cells at a target site in a mammal comprising conditioning the cells to provide cells having an altered number of adhesion molecules as compared to corresponding cells not subjected to the conditioning, wherein the conditioning increases the probability of engraftment of the cell at the target site; and delivering a composition comprising the conditioned therapeutic cells to the target site using a intracoronary delivery device.

In another specific embodiment of the present invention, the therapeutic cells comprise pluripotent or totipotent cells. In another specific embodiment of the present invention, the therapeutic cells comprise autologous cells, non-autologous cells, or xenogenic cells. In yet another specific embodiment of the present invention, the mammal is a human.

In one specific embodiment of the present invention, the conditioning comprises biological conditioning, chemical conditioning, mechanical conditioning, or any combination thereof.

In one specific embodiment of the present invention, the adhesion molecule is CD44, P-selectin glycoprotein ligand-1 (PSGL-1; CD 162), hematopoietic cell E-/L-selectin ligand (HCELL), E-selectin ligand-1, Very Late Antigen-4 (VLA-4; CD49d), Leukocyte Function Associated Antigen-1 (LFA-1), an integrin, such as an α4 integrin or a β2 integrin, CD31, VE-Cadherin (CD144), PECAM (CD31), vascular cell adhesion molecule-1 (VCAM-1), intercellular adhesion molecule (ICAM)-1, a selectin such as P-Selectin (CD62P), E-Selectin (CD62E), L-selectin, α4β7, Mac-1, cutaneous lymphocyte antigen, CD34, CD133, VEGF receptor 1 (flt-1/flk-2), VEGF receptor 2 (flk-1/KDR), or CXCR4.

In one specific embodiment of the present invention, the surface density of adhesion molecules on the cells is increased as a result of conditioning.

In one specific embodiment of the present invention, the conditioning comprises mechanical conditioning. In another specific embodiment of the present invention, the mechanical conditioning comprises subjecting the therapeutic cells to a mechanical shear. In another specific embodiment of the invention, the mechanical shear is induced by a programmable pump. In another specific embodiment, the mechanical shear in the range of about 5 dynes/cm$^2$ up to about 100 dynes/cm$^2$.

In another specific embodiment of the present invention, the conditioning comprises biological conditioning. In one specific embodiment of the present invention, the biological conditioning comprises contacting the cell with at least one chemokine.

In one specific embodiment of the present invention, the chemokine is Il-1beta, TNF-alpha, IL-4, IL-8, SDF-1, MIP-1, MCP-1/2/3/4 or lymphoactin.

In another specific embodiment of the present invention, the biological conditioning comprises contacting the cell with at least one cytokine. In one specific embodiment of the present invention, the cytokine is a platelet derived cytokine, granulocyte colony-stimulating factor (G-CSF), oxidized LDL, tumor necrosis factor-alpha, interleukin-1, or stem cell factor (SCF).

In one specific embodiment of the present invention, the biological conditioning comprises contacting the cell with at least one growth factor. In another specific embodiment of the present invention, at least one growth factor is VEGF, FGF, Insulin Growth Factor (IGF), bFGF, Hepatocyte Growth Factor, acidic fibroblast growth factor, fibroblast growth factor-4, fibroblast growth factor-5, epidural growth factor, or platelet-derived growth factor.

In one specific embodiment of the present invention, the biological conditioning comprises contacting the cell with PR39, HIF 1 alpha, HIF 2 alpha, Insulin Growth Factor (IGF), VEGF, bFGF, Hepatocyte Growth Factor, eNOS enhancers, P38 inhibitors, statins or S1P agonists.

In another specific embodiment of the present invention, the biological conditioning comprises contacting the cell with an exogenous agent. In one specific embodiment of the present invention, the exogenous agent comprises a biological conjugate, linker, or an expression cassette encoding an adhesion molecule gene product.

In a specific embodiment of the present invention, the biological conditioning comprises subjecting the cells to periods of hypoxia.

In one specific embodiment of the present invention, the conditioning comprises chemical conditioning. In one specific embodiment of the present invention, the chemical conditioning comprises conjugating a molecule or molecular moiety to the surface of the cell. In another specific embodiment, the chemical conditioning comprises attaching a molecule or molecular moiety to the surface of the cell. In one specific embodiment of the present invention, the chemical conditioning comprises contacting the therapeutic cells with at least one irritant. In another specific embodiment of the present invention, the chemical conditioning comprises contacting the therapeutic cells with at least one stimulant.

In one specific embodiment of the present invention, the composition further comprises a viscous agent. In one embodiment of the invention, the viscous agent is tocopherol, a lipid emulsion such as an emulsified vegetable oil, a surfactant, a hydrophilic polymer, or any combination thereof.

In a specific embodiment of the invention, the composition further comprises an activated platelet or a platelet-derived microparticle. In another specific embodiment of the invention, the composition further comprises a calcium ionophore, oleic acid, histamine, DMSO, histamine, bradykinin, serotonin, thrombin, VEGF, a leukotriene or a vasodilator. In a specific embodiment of the invention, the vasodilator is an ACE inhibitor or a nitrate.

In another specific embodiment of the present invention, the composition further comprises at least one agent that increases bumping frequency. In one specific embodiment of the present invention, the agent to increase the bumping frequency is a microbubble, a liposome, a lipid vesicle, a vesicle with membranes formed from di-block or tri-block co-polymers, a platelet-derived microparticle, or a microparticle.

In one specific embodiment of the present invention, the conditioning comprises contacting the cells with a magnetically responsive particle. In another specific embodiment of the invention, further comprising applying an external magnetic field gradient to the mammal following delivery of the composition. In a specific embodiment of the present invention, the magnetic particle is labeled. In one embodiment of the invention, the magnetic particle is labeled with CD44, P-selectin glycoprotein ligand-1 (PSGL-1; CD 162), hematopoietic cell E-/L-selectin ligand (HCELL), E-selectin ligand-1, Very Late Antigen-4 (VLA-4; CD49d), Leukocyte Function Associated Antigen-1 (LFA-1), an integrin, such as an α4 integrin or a β2 integrin, CD31, VE-Cadherin (CD144), PECAM (CD31), vascular cell adhesion molecule-1 (VCAM-1), intercellular adhesion molecule (ICAM)-1, a selectin such as P-Selectin (CD62P), E-Selectin (CD62E), L-selectin, α4β7, Mac-1, cutaneous lymphocyte antigen, CD34, CD133, VEGF receptor 1 (flt-1/flk-2), VEGF receptor 2 (flk-1/KDR) or CXCR4.

In one specific embodiment of the present invention, the composition further comprises a gaseous agent. In a specific embodiment of the present invention, the gaseous agent induces transient, localized ischemia at the target site. In another embodiment of the present invention, the gaseous agent is carbon dioxide.

In one specific embodiment of the present invention, the invention further comprises conditioning cells associated with the target site to provide target cells having an altered number of adhesion molecules as compared to corresponding target cells not subjected to the conditioning, wherein the conditioning increases the probability of engraftment of the therapeutic cells at the target site.

In one specific embodiment of the present invention, the composition further comprises a pharmaceutically acceptable carrier. In one specific embodiment of the present invention, the therapeutic cells are delivered after the cells are conditioned.

In a specific embodiment, the present invention provides a method of enhancing engraftment of a therapeutic cell at a target site in a mammal comprising delivering a composition comprising the therapeutic cell and one or more engraftment enhancing agents, wherein the composition is delivered to the target site using an intercoronary delivery device. In one specific embodiment of the present invention, at least one engraftment enhancing agent is gaseous and provides transient, localized ischemia at the target site. In one specific embodiment of the present invention, the gaseous engraftment enhancing agent is carbon dioxide.

In another specific embodiment of the present invention, at least one engraftment enhancing agent is a viscous agent. In one specific embodiment of the present invention, the viscous agent is tocopherol, a lipid emulsion such as an emulsified vegetable oil, a surfactant, a hydrophilic polymer, or any combination thereof.

In one specific embodiment of the present invention, at least one engraftment enhancing agent is a bumping agent.

In one specific embodiment of the present invention, at least one engraftment enhancing agent is an activated platelet or a platelet-derived microparticle. In one specific embodiment of the present invention, at least one engraftment enhancing agent is a calcium ionophore, oleic acid, histamine, DSMO, a vasodilator or any combination thereof. In one specific embodiment of the present invention, the vasodilator is an ACE inhibitor or a nitrate.

In one specific embodiment of the present invention, at least one engraftment enhancing agent is an agent that increases bumping frequency. In one specific embodiment of the present invention, the agent to increase the bumping frequency is a microbubble, a liposome, a lipid vesicle or a vesicle with membranes formed from di-block or tri-block co-polymers.

In one specific embodiment of the present invention, at least one engraftment enhancing agent is a chemokine. In another specific embodiment of the present invention, the chemokine is IL-1β, TNF-α, IL-4, IL-8, SDF-1, MIP-1, MCP-1/2/3/4 or lymphoactin. In a specific embodiment of the present invention, the chemokine is SDF-1.

In one specific embodiment of the present invention, at least one engraftment enhancing agent is a cytokine. In a specific embodiment of the present invention, the cytokine is a platelet derived cytokine, granulocyte colony-stimulating factor (G-CSF), oxidized LDL, tumor necrosis factor-alpha, interleukin-1, or stem cell factor (SCF).

In one specific embodiment of the present invention, at least one engraftment enhancing agent is a growth factor. In yet another specific embodiment of the present invention, at least one growth factor is VEGF, FGF Insulin Growth Factor (IGF), bFGF, Hepatocyte Growth Factor, acidic fibroblast growth factor, fibroblast growth factor-4, fibroblast growth factor-5, epidermal growth factor, or platelet-derived growth factor.

In one specific embodiment of the present invention, at least one engraftment enhancing agent is a magnetically responsive particle. In one specific embodiment of the present invention, the invention further comprises modifying the target site to include magnetically responsive particles.

In one specific embodiment of the present invention, the invention further comprises applying an external magnetic field gradient to the mammal following delivery of the composition. In one specific embodiment of the present invention, the magnetic particle is labeled. In one specific embodiment of the present invention, the magnetic particle has a receptor for CD34, CD133, CD44, P-selectin glycoprotein ligand-1 (PSGL-1; CD 162), hematopoietic cell E-/L-selectin ligand (HCELL), E-selectin ligand-1, Very Late Antigen-4 (VLA-4; CD49d), Leukocyte Function Associated Antigen-1 (LFA-1), an integrin, such as an $\alpha 4$ integrin or a $\beta 2$ integrin, CD31, VE-Cadherin (CD144), VEGF receptor 2 (KDR), CXCR4, $\alpha 4\beta 7$, Mac-1, or cutaneous lymphocyte antigen.

In another specific embodiment, the invention provides a method of enhancing engraftment of a therapeutic cell at a target site in a mammal comprising delivering a composition comprising the therapeutic cell and one or more engraftment enhancing agents, wherein the composition is delivered to the target site using an implantable delivery device, and wherein the one or more engraftment enhancing agents is biocompatible and provides transient, localized ischemia at the target site.

In one specific embodiment of the present invention, the biocompatible engraftment enhancing agent is a liposome.

In one specific embodiment, the present invention provides a method of enhancing engraftment of a therapeutic cell at a target site in a mammal comprising delivering a composition comprising the therapeutic cell and one or more engraftment enhancing agents, wherein the composition is delivered to the target site using an implantable delivery device, and wherein the one or more engraftment enhancing agents is biodegradable and provides transient, localized ischemia at the target site.

In one specific embodiment of the present invention, the biodegradable engraftment enhancing agent includes a microsphere or a microbubble. In another embodiment, the microsphere is made of polycaprolactone, PLGA poly(lactide-co-glycolide), polyester-amide, polyphosphazine, or tyrosine carbonate.

In one specific embodiment of the present invention, the microsphere is made of alginate crosslinked with divalent Ca, Ba or Sr cations.

In one specific embodiment of the present invention, the microsphere comprises an extra-cellular matrix protein crosslinked with glutaraldehyde.

In one specific embodiment, the present invention provides a method of enhancing engraftment of a therapeutic cell at a target site in a mammal comprising subjecting the therapeutic cell to in vitro conditioning, wherein the conditioning increases the probability of engraftment of the therapeutic cell at the target site, and delivering a composition comprising the conditioned therapeutic cell, wherein the composition is delivered to the target site using an implantable delivery device.

In one specific embodiment, the present invention provides a catheter comprising a catheter body having a dual lumen, a mixing chamber at a terminus of the catheter body, the mixing chamber having an outlet, a porous material coupled to a first lumen to generate bubbles within the mixing chamber, a discharge port coupled to the second lumen to introduce a cell into the mixing chamber, and a bypass port to admit blood into the mixing chamber.

In one specific embodiment of the present invention, the first lumen is configured to receive a gas. In another specific embodiment of the present invention, also included is a pump configured to generate the bubbles within the mixing chamber at a first predetermined time.

In one specific embodiment of the present invention, the catheter includes a pump configured to deliver the cell to the mixing chamber at a second predetermined time. In another specific embodiment of the present invention, the porous material includes a sponge.

In one specific embodiment, the present invention provides a method comprising inducing ischemia at a target site for a transitory period of time, delivering a therapeutic cell and a viscous agent to the target site, the viscous agent selected to increase a viscosity of the injection medium of the therapeutic cell, and restoring normal blood flow to the target site.

In one specific embodiment of the present invention, inducing ischemia includes introducing a flow resistor. In one specific embodiment of the present invention, inducing ischemia includes delivering an irritant or stimulant to the target site.

In one specific embodiment of the present invention, the viscous agent includes at least one of microspheres, PEG, vitamin E, PVA, PVP, dextran, and dextran sulfate.

In one specific embodiment, the present invention provides a method of delivering a therapeutic cell to a target site in a mammal comprising introducing a solution including the therapeutic cell and an agent, wherein the agent is tailored to enhance engraftment of the therapeutic cell to the target site, and wherein the solution is introduced using an implantable catheter.

In one specific embodiment of the present invention, the agent induces transient, localized ischemia at the target site. In one specific embodiment of the present invention, the agent includes at least one of a microparticle, a liposome and a $CO_2$ bubble.

In one specific embodiment, the present invention provides a method comprising modifying a target cell to upregulate an adhesion molecule counter-receptor, subjecting a therapeutic cell to mechanical conditioning so as to provide an increased number of adhesion molecules on the cell surface as compared to a non-conditioned cell, and delivering the therapeutic cell to the site of the target cell.

In one specific embodiment of the present invention, the modifying includes inducing ischemia.

In one specific embodiment of the present invention, inducing ischemia includes introducing a flow resistor in a vessel coupled to the target site.

In one specific embodiment of the present invention, shearing includes agitating with a fluid pump.

In one specific embodiment, the present invention provides a method comprising combining a magnetic particle and a therapeutic cell, applying a static magnetic field to a target site of a mammal, the static magnetic field having a gradient oriented in a direction normal to a vessel wall at the target site, and introducing the therapeutic cell.

In one specific embodiment, the present invention provides a method of enhancing engraftment of therapeutic cells at a target site in a mammal comprising contacting the therapeutic cells with a biological linker, wherein at the linker is attached to the cell membrane of a therapeutic cell, and wherein at least one functionality of the linker molecule has affinity to the surface of the therapeutic cell, and wherein at least one other functionality of the linker has affinity to the surface of the lumen surface of the target area vasculature.

In one specific embodiment of the present invention, the linker is irreversibly attached to the therapeutic cell. In one specific embodiment of the present invention, the linker is reversibly attached to the therapeutic cell.

In one specific embodiment of the present invention, the linker is a biological conjugate.

In one specific embodiment of the present invention, the linker is a multifunctional linker. In one specific embodiment of the present invention, the linker is a bi-functional linker.

In one specific embodiment of the present invention, the linker molecule comprises at least one of an antibody, an antibody fragment, a peptide, or an affibody.

In one specific embodiment of the present invention, the functionalities may be separated by a spacer. In one specific embodiment of the present invention, the spacer is a hydrophilic polymer chain. In one specific embodiment of the present invention, the spacer is PEG. In one specific embodiment of the present invention, the spacer has branches or is of star form.

In one specific embodiment of the present invention, the linker comprises linked antibodies, fragments of antibodies ($F_{ab}$ fragments), affibodies, peptides or other molecules with affinity to receptor molecules on the target surface.

II. Therapeutic Cells of the Invention

A. Sources of Therapeutic Cells for Cell Therapy

Sources for therapeutic cells in cell-based therapies include adult, neonatal and embryonic sources. Adult cells may be derived from various organs, such as skeletal muscle derived cells, for instance, skeletal muscle cells and skeletal myoblasts; cardiac derived cells, myocytes, e.g., ventricular myocytes, atrial myocytes, SA nodal myocytes, AV nodal myocytes; bone marrow-derived cells or umbilical cord derived cells, e.g., mesenchymal cells and stromal cells; smooth muscle cells; fibroblasts; or pluripotent cells or totipotent cells, e.g., teratoma cells, hematopoietic stem cells, for instance, cells from cord blood and isolated CD34$^+$ cells, multipotent adult progenitor cells, adult stem cells and embyronic stem cells. For example, progenitor cells (derived from bone marrow or circulating blood) are capable of differentiating into myocytes. Progenitor cells can be used to restore cardiac function in patients with acute or chronic damage to myocardium. For example, intracoronary treatment of acute myocardial infarct patients using progenitor cells has provided improved left ventricle ejection fraction. In one embodiment, the therapeutic cells are autologous cells. In another embodiment, the therapeutic cells include non-autologous cells, such as allogenic cells. In yet another embodiment, the therapeutic cells include xenogenic cells. The therapeutic cells can be expanded in vitro to provide an expanded population of therapeutic cells for administration to a recipient. In addition, therapeutic cells may be treated in vitro to induce one or more desirable gene products (transgenes) to the cells. For example, cells may be genetically modified to express or release chemokines and/or signal messengers when in situ. For instance, in one example the transgenic therapeutic cells include a transgene that enhances cellular engraftment, cellular proliferation, cellular survival, cellular differentiation and/or cellular function in the recipient. The transgene may be introduced to therapeutic cells by any means including but not limited to liposomes, micelles, polymeric particles, electroporation, naked DNA, plasmid or viral mediated, for instance, via an adenovirus, adeno-associated virus, retrovirus or lentivirus vector.

Sources of therapeutic cells and methods of culturing those cells are known to the art. See, for example, U.S. Pat. No. 5,130,141 and Jain et al. (*Circulation,* 103, 1920 (2001)), wherein the isolation and expansion of myoblasts from skeletal leg muscle is discussed (see also Suzuki et al., *Circulation,* 104, 1-207 (2001), Douz et al., *Circulation,* 111-210 (2000) and Zimmerman et al., *Circulation Res.,* 90, 223 (2002)). Published U.S. application 20020110910 discusses the isolation of and media for long term survival of cardiomyocytes. U.S. Pat. No. 5,580,779 discusses isolating myocardial cells from human atria and ventricles and inducing the proliferation of those myocardial cells. U.S. Pat. No. 5,103,821 discusses isolating and culturing SA node cells. For SA node cells, the cells may be co-cultured with stem cells or other undifferentiated cells. U.S. Pat. No. 5,543,318 discusses isolating and culturing human atrial myocytes. U.S. Pat. Nos. 6,090,622 and 6,245,566 discusses preparation of embryonic stem cells, while U.S. Pat. No. 5,486,359 discusses preparation of mesenchymal cells.

B. Exemplary Methods of Isolating Therapeutic Cells

1. Bone Marrow Derived Cells and Umbilical Cord Derived Cells

Therapeutic cells derived from bone marrow and umbilical cord may be prepared by protocols known in the art, for example, such as those disclosed in U.S. Pat. Nos. 5,486,359 and 5,811,094, and in U.S. Patent application publication Nos. 20050008624, 20040136967.

2. Therapeutic Myoblasts and Myocytes a. Cardiac Tissue

Cardiomyocytes may be prepared by a modification of established methods. In particular, primary myocardial cell isolation is done by modifying established protocols by Nag and Chen, *Tissue Cell,* 13, 515 (1981) and Dlugaz et al., *J. Cell Biol.,* 99, 2268 (1984). Briefly, a heart, e.g., from an organ therapeutic, is dissected and washed in media. Digestion media includes modified Jolicks MEM containing 10 mM HEPES, 10 mM pyruvate, 5 mM L-glutamine, 1 mM nicotinamide, 0.4 mM L-ascorbate, 1 mM adenosine, 1 mm D-ribose, 1 mM $MgCl_2$, 1 mM taurine, 2 mM DL-carnitine, and 2 mM $KHCO_3$. The hearts are minced in digestion media with 0.5 mg/ml collagenase (Worthington) and 100 mM $CaCl_2$. The tissue is treated with successive digestions for 15 minutes at 37° C. The cells from the first digestion are discarded and the next six digestion reactions are pooled. Cells are preplated for 1 hour to remove fibroblasts, then plated in PC-1 (Ventrex)/DME-Hams F12 media.

Alternatively, heart muscle is dissected from the left ventricular free wall and quickly cut into pieces of approximately 1 mm$^3$ using an array of razor blades. The pieces are incubated for 12 minutes, while shaking at 37° C. in 25 ml of a solution containing 1-2 µM calcium (LC) 120 mM NaCl, 5.4 mM KCl, 5 mM, $MgSO_4$, 5 mM pyruvate, 20 mM glucose, 20 mM taurine, 10 mM HEPES, and 5 mM nitrilotriacetic acid, pH 6.96. The medium is changed several (about 3) times during the twelve minutes. The pieces are stirred by bubbling with 100% $O_2$. After removal of the LC medium by straining with 300 µm gauze, the pieces are incubated at 37° C. for 45 minutes in LC without nitrilotriacetic acid, and 4 U/ml of type XXIV protease and 30 µM calcium added, followed by two 45 minute periods with the protease omitted and 400 IU/ml collagenase added. The medium is shaken under an atmosphere of 100% $O_2$. At the end of the second and third 45 minute periods, the solution containing the dispersed cells is filtered through a 300 μm gauze and centrifuged at 40×g for 1-2 minutes.

Alternatively, primary ventricular myocytes and cardiac fibroblasts are prepared using a Percoll gradient method as described by Iwaki et al., *J. Biol Chem.*, 265, 13809 (1990). Cardiac fibroblasts are isolated from the upper band of the Percoll gradient, and subsequently plated in high glucose Dulbecco's modified Eagle's medium supplemented with 10% fetal bovine serum. Myocytes are isolated from the lower band of the Percoll gradient and subsequently plated in 4:1 Dulbecco's modified Eagle's medium; 199 medium, 10% horse serum and 5% fetal bovine serum.

After isolation, the cells may be washed in a medium containing calcium, e.g., 30 μM calcium, and resuspended in culturing media. Such culture media can comprise DMEM, BSA, ascorbic acid, taurine, carnitine, creatinine, insulin, penicillin G sodium, and an antibiotic, e.g., DMEM with the addition of 0.2 g BSA, 0.1 mM ascorbic acid, 50 mM taurine, 16 mM carnitine, 50 mM creatine, 0.1 μM insulin, 50 U/ml penicillin G sodium, and 50 mg/ml streptomycin sulfate. Culture media can also comprise DMEM without calcium chloride anhydrous and D-calcium pantothenate.

Omega 3 fatty acids have been shown by Kang & Leaf (*Circulation*, 94, 1774 (1996)) to protect against calcium overload and calcium paradox. Therefore, the culture media may also comprise omega 3 fatty acids, such as, docosaheanoic acid, eicosapentaenoic acid, eicosatetraynoic acid, or polyunsaturated fatty acid.

Magnesium ($Mg^+$) is also known to be protective against calcium overload and has been shown to be beneficial in failing human myocardium (Schwinger et al., *Am. Heart J.*, 126, 1018 (1993); Schwinger et al., *J. Pharmacol. Exp. Ther.*, 263, 1352 (1992)). Therefore, the culture media may comprise varying concentrations of $Mg^{2+}$, e.g., from 0.1 to 16 mM.

In one embodiment, cardiomyocytes are obtained from a tissue sample from a subject, e.g., a vertebrate subject, and successively exposed to a first solution with decreasing amounts of $CaCl_2$. The first solution further includes NaCl, HEPES, $MgCl_2$, KCl, and sugar at a pH of approximately 7.4, e.g., 140 mM NaCl, 10 mM HEPES, 1 mM $MgCl_2$, 5.4 mM KCl, and 10 mM sugar at a pH of approximately 7.4. The tissue may be disassociated with an enzyme solution and repeatedly resuspended in a second solution with increasing amounts of $CaCl_2$. The second solution may further include Earle's modified salt, L-glutamine, sodium bicarbonate, sodium pentothenate, creatine, taurine, ascorbic acid, HEPES, fetal bovine serum, an antibiotic, and a fatty acid, at a pH of approximately 7.4, e.g., sodium bicarbonate at 1250 mg/l, creatine at 328 mg/500 ml, taurine at 312 mg/500 ml, ascorbic acid at 8.8 mg, HEPES at 2.383 g/500 ml, fetal bovine serum at 10% v/v, an antibiotic at 5% v/v, and a fatty acid at 1 μM at a pH of approximately 7.4.

In yet another embodiment, the second solution can be used to cultivate isolated cells, e.g., cardiomyocytes, including the steps of resuspending the isolated cells approximately every 24 hours in the second solution. In still another embodiment, the second solution can be used as maintenance or culture media for cells, e.g., cardiomyocytes.

In another embodiment, cardiomyocytes are obtained from a tissue sample from a subject, e.g., a vertebrate subject, by cutting the tissue into smaller pieces and incubating the tissue in a first solution. The first solution includes calcium, salts, magnesium sulfate, pyruvate, glucose, taurine, HEPES, and nitrilotriacetic acid, e.g., 1-2 μM $CaCl_2$, 120 mM NaCl, 5.4 mM KCl, 5 mM $MgSO_4$, 5 mM pyruvate, 20 mM glucose, 20 mM taurine, 10 mM HEPES, and 5 mM nitrilotriacetic acid, at a pH of approximately 6.96. After the addition of an enzyme, e.g., collagenase, to the first solution, the tissue is further incubated in the solution and later subjected to centrifugation to obtain isolated cells. After shaking the tissue at 37° C. for 12 minutes, and bubbling 100% $O_2$ through the solution, the tissue is incubated in a second solution comprising 1-2 μM $CaCl_2$, 30 μM NaCl, 5.4 mM KCl, 5 mM $MgSO_4$, 5 mM pyruvate, 20 mM glucose, 20 mM taurine, 10 mM HEPES, and 4 U/ml of a digestive enzyme, and subsequently incubated in a third solution comprising approximately 1-2 μM, 30 μM NaCl, 5.4 mM KCl, 5 mM $MgSO_4$, 5 mM pyruvate, 20 mM glucose, 20 mM taurine, 10 mM HEPES, and 4 U/ml of a digestive enzyme. Preferably, 400 U/ml of a digestive enzyme, e.g., a type XXIV protease, such as matrix metalloproteinase 2 or 4, and a collagenase, for example, matrix metalloproteinase 1, 3, or 9, is added to the third solution and the tissue subjected to centrifugation to obtain isolated cells.

Other solutions to enhance the yield and long-term survival rate of isolated cardiomyocytes include those in published U.S. application 20020110910.

b. Neonatal Skeletal Tissue

To harvest cells from neonatal tissue, muscle tissue is harvested from a limb and placed in a culture dish (65 mm diameter) with 8 ml of calcium-free PBS. Muscles are removed under sterile conditions. All harvested tissue is transferred to a 50 ml conical tube containing 12 ml of tissue dissociation solution (TDS) (DMEM with 5% by weight dispase and 0.5% by weight collagenase IV) and stirred for approximately one hour in order to dissociate the tissue. The tube is then centrifuged at 1200×g for approximately 15 minutes. After removal of the supernatant, cells are resuspended in 20 ml of Ham's F12 with 20 mg of collagenase type IV and incubated at 37° C. for one hour to allow tissue dissociation. The tube is again centrifuged at 1200 g for 15 minutes, after which the supernatant is removed and the cells are resuspended in growth media (GM) (400 ml F12, 100 ml FBS and 100 U/ml penicillin G). Within this cell suspension will likely be fibroblasts in addition to myogenic precursor cells.

c. Adult Skeletal Tissue

Skeletal muscle may also be harvested from adult tissue and cut into strips. Unlike neonatal tissue, muscle tissue from adult or aged animals yields more satellite cells if initially preincubated before complete tissue dissociation. The increased activation of satellite cells may result from the use of $NaN_3$ in the preincubation media (PI) (90 ml DM and 10 ml 0.05% $NaN_3$ in 0.9% saline, where DM is 465 ml DMEM, 35 ml horse serum and 100 U/ml penicillin G).

To preincubate the muscle tissue, the strips are pinned in a SYLGARD™ coated culture dish (35 mm diameter), covered with 2.5 ml of PI, and sterilized by exposure to ultraviolet light for approximately 40 minutes. The dishes are then maintained at 37° C. in a water-saturated atmosphere containing 5% $CO_2$ for 24 to 72 hours, where optimal pre-incubation times may vary for different muscles.

After pre-incubation, each muscle strip is placed into a 50 ml conical tube with 15 ml TDS solution and incubated in a shaker bath at 37° C. for approximately 3 hours until complete dissociation is observed. Immediately upon complete tissue dissociation, the tubes are centrifuged at 1200 g for 15 minutes. Subsequently, the supernatant is aspirated and cells are reconstituted with 5 ml GM. As with the cells derived from neonatal tissue, fibroblasts may be included in the cell suspension.

Alternatively, myogenic cells are released from skeletal muscle fragments by serial enzyme treatments. A one hour digestion with 600 U/ml collagenase (Sigma, St. Louis, Mo., USA), is followed by a 30 minute incubation in Hank's balanced salt solution (HBSS) containing 0.1% w/v trypsin (Gibco Lab, Grand Island, N.Y., USA). Satellite cells are placed in 75 cm² culture flasks (Coster, Cambridge, Mass., USA) in proliferation medium, e.g., 199 medium (Gibco Lab.) with 15% fetal bovine serum (Gibco), 1% penicillin (10,000 U/ml) and 1% streptomycin (10,000 U/ml).

In particular, for human myoblasts, these cells are grown from therapeutic human muscle and passaged cells are seeded at 2-3,000 cells per well in a 96 well cluster plate in Ham F12 medium containing 7.5% up to 20% v/v FCS. The medium may contain varying concentrations of LIF. Cell numbers are counted at times up to 12 days. There is a marked stimulation of proliferation of myoblasts by LIF, e.g., at 30 U/ml. FGF and HBGF also stimulate growth of satellite cells (DiMario et al., *Differentiation*, 39, 42 (1988)). TGF-α also stimulates human cells at concentrations ranging up to 10 ng/ml.

In one embodiment, to expand skeletal muscle cells, skeletal muscle cells are cultured with isolated PDGF, TGF-beta, and/or FGF, e.g., at 5-10 ng/ml.

d. Non-Muscle Therapeutic Cells

Methods to isolate and/or culture non-muscle therapeutic cells, and methods to induce a muscle cell-specific phenotype to those cells, i.e., differentiation, are known to the art. For instance, mesenchymal stem cells may be obtained by culturing adherent marrow or periosteal cells.

To induce a cardiac cell-specific phenotype, MSCs cells may be cocultured with fetal, neonatal or adult cardiac cells optionally in the presence of fusigens, extracts of mammalian hearts, one or more growth factors, one or more differentiating agents, or subjected to mechanical or electrical stimulation.

Bone marrow is a source for therapeutic cells that have the potential to differentiate into cardiomyocytes, endothelial cells, in the case of endothelial progenitor cells, and smooth muscle cells (see, for example, Yoon et al., *J. Clin. Invest.*, 115:326-338 (2005)). To obtain bone marrow cells, a bone marrow puncture is conducted by sternal or iliac puncture. After skin disinfection of the part for puncture, a therapeutic is subjected to local anesthesia. Particularly, subpeiosteum is thoroughly anesthetized. The inner tube of a bone marrow puncture needle is pulled out and a 10 ml syringe containing 5000 U of heparin is attached to the needle. Normally 10-20 ml of the bone marrow fluid is quickly taken by suction and the puncture needle is removed, followed by pressure hemostasis for about 10 minutes. The obtained bone marrow fluid is centrifuged at 1000×g to recover bone marrow cells, which are then washed with PBS (phosphate buffered saline). After this centrifugation step is repeated twice, the obtained bone marrow cells are suspended in a cell culture medium such as A-MEM (a-modification of MEM), DMEM (Dulbecco's modified MEM) or IMDM (Isocove's modified Dulbeccos's medium) each containing 10% FBS (fetal bovine serum) to prepare a bone marrow cell suspension.

For the isolation of the bone marrow cells having the potential to differentiate into cardiomyocytes from the obtained bone marrow cell suspension, any method can be employed, so long as it is effective at removing other cells existing in the cell suspension such as hematocytes, hematopoietic stem cells, vascular stem cells and fibroblasts. For example, based on the method described in Pittenger et al., *Science*, 284, 143 (1999), the desired cells can be isolated by subjecting the cell suspension layered over Percoll having the density of 1.073 g/ml to centrifugation at 1100×g for 30 minutes, and the cells on the interface are recovered. Furthermore, a bone marrow cell mixture containing the cells having the potential to differentiate into cardiomyocytes can be obtained by mixing the above cell suspension with an equal amount of Percoll solution diluted to 9/10 with 10×PBS, followed by centrifugation at 20000×g for 30 minutes, and recovering the fraction having the density of 1.075-1.060. A bone marrow cell mixture is diluted into single cell using 96-well culture plates to prepare a number of clones respectively derived from single cells. The clones having the potential to differentiate into cardiomyocyte can be selected by the observation of spontaneously beating cells generated by the treatment.

For the isolation of the bone marrow cells having the potential to differentiate into endothelial cells from the obtained bone marrow cell suspension, the method described by Asahara et al., *Science*, 275: 964-967 (1997) or Asahara et al., *Circulation Research*, 85:221-228 (1999)) might be employed.

Umbilical blood is another source for therapeutic cells. To prepare those cells, umbilical blood is separated from the cord, followed by addition of heparin to give a final concentration of 500 U/ml. After thoroughly mixing, cells are separated from the umbilical blood by centrifugation and resuspended in a cell culture medium, such as α-MEM, DMEM or IMDM, each containing 10% FBS. From the cell suspension thus obtained, cells having the potential to differentiate into cardiomyocytes can be separated using, for example, antibodies.

Fibroblasts are also a source for therapeutic cells.

$CD34^+$ cells may be obtained from a population of other cells, e.g., from blood cells when $CD34^+$ cells are isolated from blood or cord blood, by cell labeling with magnetic antibodies and subsequent cell separation in a magnetic field. For example, cells may be separated by using a commercially available cell selection system, such as CliniMACS® (Miltenyi Biotec GmbH).

C. Conditioning Therapeutic Cells to Enhance Engraftment at Target Site

As disclosed herein, the surface of therapeutic cells, e.g., stem cells, may be modified to increase the probability or strength of attachment to the lumen surface of the target area (e.g., endothelium). A variety of exogenous stimuli ("conditioning") may be employed in the methods to enhance engraftment, increase the probability or strength of attachment of the therapeutic cells to the target site. For instance, therapeutic cells may be treated in vitro or in vivo by subjecting them to mechanical conditioning, biological conditioning, chemical conditioning, or any combination thereof. The conditioning may include continuous or intermittent exposure to the exogenous stimuli. Exogenous agents include those that enhance the attachment, engraftment, survival, differentiation, proliferation and/or function of therapeutic cells, e.g., stem cells, after transplant to the luminal surface of the target area, e.g., endothelium. For example, the surface of a therapeutic cell can be modified in such a way that the surface density of available adhesion molecules is altered, e.g., increased, wherein the adhesion molecule possesses an affinity to the luminal surface of the target area vasculature, e.g., to a corresponding adhesion molecule present on or associated with the cell surface of an endothelial cell or molecular moieties thereon. In one example, adhesion molecules have an affinity to the luminal surface of the target vasculature and are antibodies to receptor molecules present on the surface of the endothelial cells (for example, anti-CD31 or anti-ICAM). Examples of such conditioning are disclosed herein. In another example, platelet factor 4 (PF4) is used to upregulate the expression of CD(49d) and CXCR4 on therapeutic cells, which affects cell adhesion and enhance engraftment at a target site. Lu et al., *Zhonghua Xue Ye Xue Za Zhi*, 24: 467-469 (2003).

1. Mechanical Conditioning

As disclosed herein, therapeutic cells may be influenced in a manner similar to other cell types such as endothelial cells and lymphocytes to improve cell engraftment levels.

As used herein, the phrase "mechanical conditioning" refers to a mechanical process that results in the alteration of surface density, gene expression, protein synthesis, and/or the activity of one or more adhesion molecules on the therapeutic cells. For example, exposure of endothelial progenitor cells to shear stress increases the expression of vascular endothelial cadherin. Yamamoto et al., *J. Appl. Physiol.*, 95: 2081-2088 (2003). See also Peled et al., *J. Clin. Invest.*, 104: 1199-1211 (1999) and Rood et al., *Exp. Hematol.*, 27: 1306-1314 (1999). Thus, in one embodiment, the mechanical conditioning of the therapeutic cells, e.g., stem cells, results in the expression and/or upregulation of the expression of adhesion molecules that facilitate the retention of the therapeutic cells to the vascular endothelium.

In one embodiment, the mechanical conditioning of therapeutic cells results in the enhanced engraftment of the therapeutic cells at the target site. For example, therapeutic cells, such as stem cells, may be exposed to controlled shear rates through a shear module consisting of the pre-determined length of tubing connected to a controlled flow rate pump. Exposing therapeutic cells to any positive shear stress, for example, in the range of about 5 dynes/cm$^2$ up to about 100 dynes/cm$^2$, may be useful to upregulate expression of an adhesion molecule. In addition to shearing cells before delivery, saline fluid can be used to mechanically condition the therapeutic cells.

Views of an exemplary shear module are illustrated FIGS. 1A, 1B and 1C. For example, FIG. 1A illustrates shear module 100 having pump 110, flow cartridge 130 and collection syringe 140. Pump 110 is illustrated as a syringe pump, however other types of pumps are also contemplated including, for example, vane pumps, diaphragm pumps and gear pumps. Pump 110 delivers cell suspension 120 to flow cartridge 130 in a controlled manner. Discharge from flow cartridge 130 is received by collection syringe 140. Syringe 140 can be coupled, for example, to stem cell delivery apparatus (not shown). Collection syringe 140, for example, can be a syringe having a volume of between 1 and 10 cc.

FIG. 1B illustrates a cut-away view of flow cartridge 130. Flow cartridge 130 receives cell suspension 120 at input port 131 and discharges cell suspension at output port 133. A plurality of channels, each marked 132, serve to control fluid flow through flow cartridge 130. FIG. 1C illustrates a cross-sectional view of flow cartridge 130 having a plurality of circular channels 132 disposed about the interior. Cell suspension 120 entering at port 131 is sheared by the flow process through channels 132. Each of channel 132, in one example, includes a plastic tube having a diameter of between 100 and 500 microns. An exemplary material for channel 132 includes polystyrene. Dimensions and materials other than those described herein are also contemplated.

Expression profiles of adhesion molecules can also be manipulated by the magnitude and type of shear stress, i.e., laminar v. turbulent, and time of exposure to the shear stress. Any mechanism that induces shear stress might be utilized in the mechanical conditioning of the therapeutic cells.

In one example, the present subject matter provides methods and systems for modifying the cells ex vivo (prior to delivery at the site), such as in a catheter laboratory to improve cell engraftment.

2. Biological Conditioning

In addition to mechanical conditioning, therapeutic cells can be subjected to biological conditioning to enhance the engraftment at a target site. For example, brief periods of incubation (e.g., 4-6 hours) of therapeutic cells with chemokines such as Il-1beta, TNF-alpha and IL-4 induces upregulation of E-selectin, ICAM-1 and VCAM-1 on endothelial cells (Konstantopoulos et al., *Advanced Drug Delivery Reviews*, 33:141-164 (1998)). Cells can be contacted with chemokines for a determined period of time (e.g., about 1 hour to about 24 hours), washed to remove the residual chemokines, and then infused into the patient. Other biological conditioning agents include, but are not limited to, PR39, HIF 1 alpha, HIF 2 alpha, Insulin Growth Factor (IGF), VEGF, bFGF, Hepatocyte Growth Factor, eNOS enhancers, P38 inhibitors, statins and S1P agonists.

In addition, biological conditioning includes subjecting therapeutic cells to exogenous agents, such as biological conjugates, linkers, as well as to expression cassettes (transgenes) encoding a gene product including, but not limited to, an adhesion molecule.

In another embodiment, therapeutic cells are subjected to periods of hypoxia to upregulate adhesion molecules. For example, cells may be incubated in a portable hypoxic chamber for periods of time, for example, 30 minutes to 24 hours, before delivery into the patient.

a. Biological Conjugates and Linkers

The modification of proteins by labeling with reporter molecules is known in the art. Therapeutic cells can be contacted with biological linkers, such as biologically active entities irreversibly attached to the therapeutic cell (see for example, Krantz, *Blood Cells, Molecules and Diseases*, 23:58-68 (1997) and/or biological conjugates, such as bifunctional antibody constructs. Alternatively, biological linkers may be attached through a reversible bond where the time scale of dissociation is sufficiently long to mediate adhesion between therapeutic and target cells.

Figure 1D:
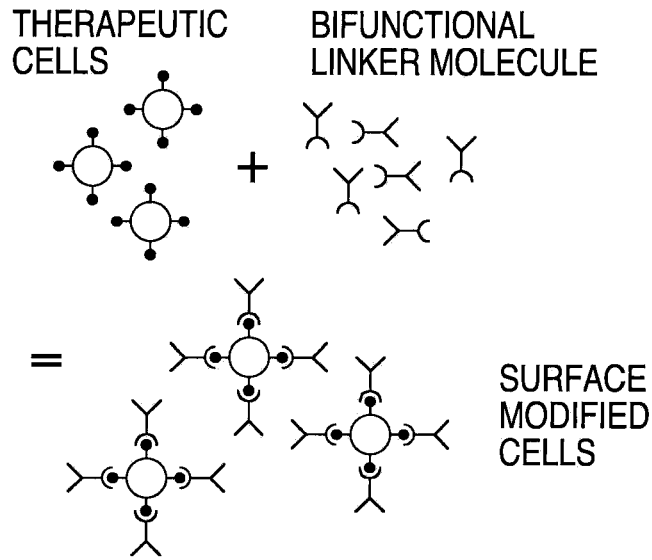
FIG. 1D illustrates surface modified therapeutic cells.
Figure 1E:
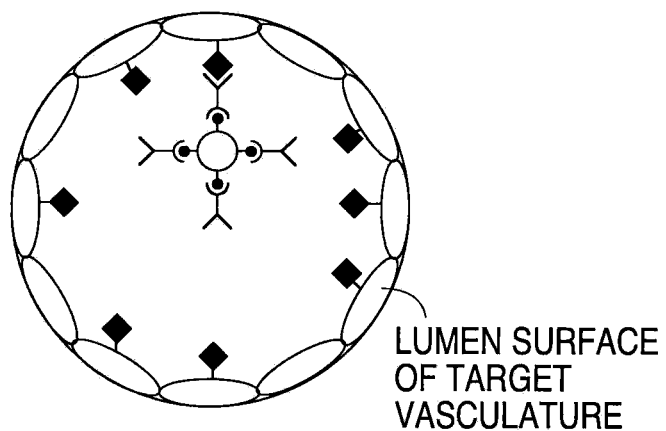
FIG. 1E illustrates a therapeutic cell attached to a lumen surface by a bi-functional linker molecule.

In one embodiment, the biological conjugate includes but is not limited to a bi- or multifunctional linker. For example, bi- or multifunctional linker molecules may be attached to the cell membrane of a therapeutic cell, where at least one functionality of the linker molecule has affinity to the surface of the therapeutic cell, and at least one other functionality has affinity to the surface of the lumen surface of the target area vasculature, e.g., endothelial cell surface, as illustrated in FIGS. 1D and 1E. FIG. 1D illustrates surface modification of therapeutic cells using bifunctional linker molecules. In the figure, the linker molecule includes anti-E and anti-T. FIG. 1E illustrates a therapeutic cell attached to an endothelial cell of the target vasculature. To enhance accessibility, the functionalities may be separated by a spacer, such as a hydrophilic polymer chain, e.g., PEG. For multifunctional linkers, the spacer may have branches or be of star form. For example, the surface of the therapeutic cell may be modified by a molecule consisting of two linked antibodies, where one antibody has affinity to a surface receptor (such as an adhesion molecule) on the therapeutic cell and where the other antibody has affinity to an endothelial surface receptor (such as an adhesion molecule). Instead of antibodies, fragments of antibodies ($F_{ab}$ fragments), affibodies (a library of proteins with a variable region with recognition capabilities similar to antibodies; as disclosed in U.S. Pat. Nos. 5,831,012, 6,534,628 and 6,740,734), peptides or other molecules with affinity to receptor molecules on the respective target surface may be used.

In one embodiment of the invention, the expression of therapeutic cells' adhesion molecules such as receptors CD34, CD133 and/or KDR, e.g., stem cells, may be altered, e.g., increased, in order to manipulate the adhesion of the therapeutic cells to target cells. For example, a CD133-antibody linked via a PEG spacer to a CD31-antibody may be used to modify the surface of a therapeutic cell, e.g., a stem cell. In this case, the CD133 antibody has affinity to the CD133 receptor present at the surface of the stem cell, while the CD31 antibody has affinity to the endothelial cell surface present on the lumen wall of the target vasculature. To modify the surface of the stem cell, the cells are incubated with a bifunctional anti-CD133-PEG-anti-CD31 molecule. As the anti-CD133 moiety attaches to the CD133 receptor, the stem cell surface will effectively present anti-CD31 antibodies with affinity to the surface of the endothelial cell found in the target vasculature. Examples of other receptor targets present on endothelial cells of microvasculature include, but are not limited to, PECAM (CD31), vascular cell adhesion molecule-1 (VCAM-1), intercellular adhesion molecule (ICAM)-1, a selectin such as P-Selectin (CD62P), E-Selectin (CD62E), L-selectin, and Flk-1, which also may be modified through bifunctional antibody construct technology. In one embodiment, the linker is an anti-CD31 or anti-ICAM antibody attached to the therapeutic cell.

b. Genetic Modification i. Transgenes

In one embodiment, a transgene is introduced into a therapeutic cell. The transgene encodes a gene product including but not limited to an adhesion molecule with an affinity for the luminal surface of the target vasculature. Adhesion molecules include, for example, CD44, P-selectin glycoprotein ligand-1 (PSGL-1; CD 162), hematopoietic cell E-/L-selectin ligand (HCELL), E-selectin ligand-1, Very Late Antigen-4 (VLA-4; CD49d), Leukocyte Function Associated Antigen-1 (LFA-1), an integrin, such as an α4 integrin or a β2 integrin, CD31, VE-Cadherin (CD144), PECAM (CD31), vascular cell adhesion molecule-1 (VCAM-1), intercellular adhesion molecule (ICAM)-1, a selectin such as P-Selectin (CD62P), E-Selectin (CD62E), L-selectin, α4β7, Mac-1, cutaneous lymphocyte antigen, CD34, CD133, VEGF receptor 1 (flt-1/flk-2), VEGF receptor 2 (flk-1/KDR), and CXCR4. The upregulation of one subset of these molecules enhances adhesion of therapeutic cells to cells associated with a target site, for example, endothelial cells, by directly increasing the surface concentration of adhesion sites, while another subset of these adhesion molecules may require additional modification, as described herein, to enhance cell engraftment.

For purposes of the present subject matter, control elements, such as promoters, enhancers and the like, will be of particular use. Such control elements include, for example, a cytomegalovirus promoter and variants thereof (commercially available from Clontech or Genetherapy Systems).

A transgenic therapeutic cell includes a transgene that enhances the engraftment, proliferation, survival, differentiation and/or function of the therapeutic cells and/or decreases, replaces or supplements (increases) the expression of endogenous genes in the therapeutic cells. In one embodiment, the expression of the transgene is controlled by a regulatable or tissue-specific, e.g., cardiomyocyte-specific promoter. Optionally, a combination of vectors each with a different transgene can be employed.

(a) Exemplary Genes for Delivery

Exemplary genes for delivery to a therapeutic cell include those genes that express adhesion molecules, as discussed herein.

(b) Delivery of Transgenes to Therapeutic Cells

Delivery of exogenous transgenes to a therapeutic cell may be accomplished by any means, e.g., transfection with naked DNA, e.g., a vector comprising the transgene, liposomes, association with polycations, calcium-mediated transformation, electroporation, or transduction, e.g., using recombinant viruses. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Feigner et al., *Proc. Natl. Acad. Sci. USA*, 84, 7413 (1987)), and nucleic acid delivery using high-velocity microprojectiles (Klein et al., *Nature*, 327, 70 (1987)).

An expression cassette optionally includes at least one control element such as a promoter, for example, a commercially available cytomegalovirus promoter, variants thereof, or optionally a regulatable promoter, e.g., one which is inducible or repressible, an enhancer, or a transcription termination sequence. In certain embodiments, the promoter and/or enhancer is one which is cell- or tissue-specific, e.g., cardiac cell-specific. For instance, the enhancer may be a muscle creatine kinase (mck) enhancer, and the promoter may be an alpha-myosin heavy chain (MyHC) or beta-MyHC promoter (see Palermo et al., *Circ. Res.*, 78, 504 (1996)).

In one embodiment, vectors are used to deliver exogenous transgenes to therapeutic cells. Vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see e.g., WO 92/08796; and WO 94/28143). Such marker genes can provide an added measure of control that can be advantageous in gene therapy contexts. A large variety of such vectors are known in the art and are generally available.

Vectors include, but are not limited to, isolated nucleic acid, e.g., plasmid-based vectors which may be extrachromosomally maintained and viral vectors, e.g., recombinant adenovirus, retrovirus, lentivirus, herpesvirus, including cytomegalovirus, poxvirus, papilloma virus, or adeno-associated virus (AAV), including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary viral vectors are described below.

Vectors are administered via intracoronary administration as described herein, and transfer to cells may be enhanced using electroporation and/or ionophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., Meth. Mol. Med., 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing cardiac specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., Nat. Med., 8:864 (2002); Lynch et al., Circ. Res., 80:197 (1997)).

In one embodiment, recombinant AAV (rAAV) is employed to deliver a transgene to therapeutic cells. Differentiation is induced by placing subconfluent therapeutic cells in DMEM containing 2% horse serum and standard concentrations of glutamine and penicillin-streptomycin for an interval of four days prior to transduction.

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes, e.g., genes encoding ryanodine receptors and titin.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, Nature, 415:234 (2002)). Furthermore, plasmid DNA is rapidly degraded in the blood stream; therefore, the change of transgene expression in distant organ systems in negligible. Plasmid DNA may be delivered to cells as part of a macromolecular complex, e.g., a liposome, polymer, e.g., cationic polymer, or DNA-protein complex, and delivery may be enhanced using techniques including electroporation.

Regulatable Transcriptional Control Elements

A variety of strategies have been devised to control in vivo expression of transferred genes and thus alter the pharmacokinetics of in vivo gene transfer vectors in the context of regulatable or inducible promoters. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16 (Ho et al., Brain Res. Mol. Brain Res., 41:200 (1996)); a chimeric promoter with multiple cyclic adenosine monophosphate response elements superimposed on a minimal fragment of the 5'-flanking region of the cystic fibrosis transmembrane conductance regulator gene (Suzuki et al., 7:1883 (1996)); the EGRI radiation-inducible promoter (Hallahan et al., Nat. Med., 1:786 (1995)); and the chimeric GRE promoter (Lee et al., J. Thoracic Cardio. Surg., 118:26 (1996)), with 5 GREs from the rat tyrosine aminotransferase gene in tandem with the insertion of Ad2 major late promoter TATA box-initiation site (Narumi et al., Blood, 92:812 (1998)). Examples of the physiologic control of promoters include a chimera of the thymidine kinase promoter and the thyroid hormone and retinoic acid-responsive element responsive to both exogenous and endogenous tri-iodothyroniine (Hayashi et al., J. Biol. Chem., 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., Cancer Res., 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., Mol. Cell Biol., 16:4604 (1996)).

Regulatable transcriptional elements include, but are not limited to, a truncated ligand binding domain of a progesterin receptor (controlled by antiprogestin), a tet promoter (controlled by tet and dox) (Dhawan et al., Somat. Cell. Mol.

*Genet.*, 21: 233 (1995); Gossen et al., *Science,* 268: 1766 (1995); Gossen et al., *Science,* 89: 5547 (1992); Shockett et al., *Proc. Natl. Acad. Sci. USA,* 92, 6522 (1995)), hypoxia-inducible nuclear factors (Semenza et al., *Proc. Natl. Acad. Sci. USA,* 88, 5680 (1991); Semenza et al., *J. Biol. Chem.,* 269, 23757)), steroid-inducible elements and promoters, such as the glucocorticoid response element (GRE) (Mader and White, *Proc. Natl. Acad. Sci. USA,* 90, 5603 (1993)), and the fusion consensus element for RU486 induction (Wang et al., *Proc. Natl. Acad,* Sci. USA, 91:818 (1994)), those sensitive to electromagnetic fields, e.g., those present in metallothionein I or II, c-myc, and HSP70 promoters (Lin et al., *J. Cell. Biochem.,* 81: 143 (2001); Lin et al., *J. Cell. Biochem.,* 54: 281 (1994); U.S. published application 20020099026)), and electric pulses (Rubenstrunk et al., *J. Gene Med.,* 5:773 (2003)), as well as a yeast GAL4/TATA promoter, auxin inducible element, an ecdysone responsive element (No et al., *Proc. Natl. Acad. Sci. USA,* 93:3346 (1996)), an element inducible by rapamycin (FK 506) or an analog thereof (Rivera et al., *Nat. Med.,* 2:1028 (1996); Ye et al., *Science,* 283:88 (1999); Rivera et al., *Proc. Natl. Acad. Sci. USA,* 96:8657 (1999)), a tat responsive element, a metal, e.g., zinc, inducible element, a radiation inducible element, e.g., ionizing radiation has been used as the inducer of the promoter of the early growth response gene (Erg-1) Hallahan et al., *Nat. Med.,* 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.,* 15:1002 (1997)), a light inducible element (Shimizu-Sato et al., *Nat. Biotech.,* 20:1041 (2002)), a lacZ promoter, and a yeast Leu3 promoter.

In some embodiments, cell- or tissue-specific control elements, such as muscle-specific and inducible promoters, enhancers and the like, will be of particular use, e.g., in conjunction with regulatable transcriptional control elements. Such control elements include, but are not limited to, those derived from the actin and myosin gene families, such as from the myoD gene family (Weintraub et al., *Science,* 251, 761 (1991)); the myocyte-specific enhancer binding factor MEF-2 (Cserjesi and Olson, *Mol. Cell Biol.,* 11, 4854 (1991)); control elements derived from the human skeletal actin gene (Muscat et al., *Mol. Cell Biol.,* 7, 4089 (1987)) and the cardiac actin gene; muscle creatine kinase sequence elements (Johnson et al., *Mol. Cell Biol.,* 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acteylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

In other embodiments, disease-specific control elements may be employed. Thus, control elements from genes associated with a particular disease, including but not limited to any of the genes disclosed herein may be employed.

Nevertheless, other promoters and/or enhancers which are not specific for cardiac cells or muscle cells, e.g., RSV promoter, may be employed. Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

Targeted Vectors

The present subject matter contemplates the use of cell targeting not only by delivery of the transgene or therapeutic cell into the coronary artery, for example, but also by use of targeted vector constructs having features that tend to target gene delivery and/or gene expression to a particular host cells or host cell types (such as the myocardium). Such targeted vector constructs would thus include targeted delivery vectors and/or targeted vectors, as described herein. Restricting delivery and/or expression can be beneficial as a means of further focusing the potential effects of gene therapy. The potential usefulness of further restricting delivery/expression depends in large part on the type of vector being used and the method and place of introduction of such vector. For instance, delivery of viral vectors via intracoronary injection to the myocardium has been observed to provide, in itself, highly targeted gene delivery. In addition, using vectors that do not result in transgene integration into a replicon of the host cell (such as adenovirus and numerous other vectors), cardiac myocytes are expected to exhibit relatively long transgene expression since the cells do not undergo rapid turnover. In contrast, expression in more rapidly dividing cells would tend to be decreased by cell division and turnover. However, other means of limiting delivery and/or expression can also be employed, in addition to or in place of the illustrated delivery method, as described herein.

Targeted delivery vectors include, for example, vectors (such as viruses, non-viral protein-based vectors, polymer-based and lipid-based vectors) having surface components (such as a member of a ligand-receptor pair, the other half of which is found on a host cell to be targeted) or other features that mediate preferential binding and/or gene delivery to particular host cells or host cell types. As is known in the art, a number of vectors of both viral and non-viral origin have inherent properties facilitating such preferential binding and/or have been modified to effect preferential targeting (see, e.g., Miller, et al., *FASEB Journal,* 9:190 (1995); Chonn et al., *Curr. Opin. Biotech.,* 6:698 (1995); Schofield et al., *British Med. Bull.,* 51: 56 (1995); Schreier, *Pharmaceutical Acta Helvetiae* 68:145 (1994); Ledley, *Human Gene Therapy,* 6:1129 (1995); WO 95/34647; WO 95/28494; and WO 96/000295).

Targeted vectors include vectors (such as viruses, non-viral protein-based vectors and lipid-based vectors) in which delivery results in transgene expression that is relatively limited to particular host cells or host cell types. For example, transgenes can be operably linked to heterologous tissue-specific enhancers or promoters thereby restricting expression to cells in that particular tissue. For example, tissue-specific transcriptional control sequences derived from a gene encoding left ventricular myosin light chain-2 ($MLC_2V$) or myosin heavy chain (MHC) can be fused to a transgene within a vector. Expression of the transgene can therefore be relatively restricted to ventricular cardiac myocytes.

Additional gene transfer methods are also contemplated, such as packaging of DNA with polycations into nanoparticles. Positively charged polycations complex spontaneously with DNA, which is negatively charged, resulting in self-assembled nanoparticles. If the DNA charge is over-compensated, the resulting particle charge is positive, which then drives the association with negatively charged cell membranes, thereby facilitating transfection. As an example of gene delivery using a polycation, see Sweeney et al., *Cancer Research*, 63: 4017-4020 (2003). Exemplary polycations include, but is not limited to, polylysine, polyethylenimine, such as in vivo-jetPEI™ (Avanti® Polar Lipids, Inc.) and protamine.

c. Exemplary Methods to Characterize the Phenotype of Therapeutic Cells Subjected to Biological Conditioning Methods to detect expression of a transgene in a therapeutic cell include methods that detect transgene-specific RNA, e.g., RT-PCR, or methods that detect a gene product encoded by the transgene, e.g., via an ELISA. Examples of gene-specific assays include, for instance, those for AC (see, Salomon et al., *Anal. Biochem.*, 58, 541 (1974); Hammond et al., *Circulation*, 85, 269 (1992); Hammond et al., *Circulation*, 8, 666 (1992)), for β-adrenergic receptor binding or content (Hammond et al., *Circulation*, 8, 666 (1992); Roth et al., *FEBS Lett.*, 29, 46 (1992)), for $GRK_2$ and $GRK_5$ content (see, e.g., Ping et al., *J. Clin. Invest.*, 95, 1271 (1995); and Roth et al., *FEBS Lett*, 29, 46 (1992)), and for G protein receptor kinase activity (see, Benovic, *Methods Enzymology*, 200, 351 (1991); Ping et al., *J. Clin. Invest.*, 95, 1271 (1995); Ping et al., *J. Clin. Invest.*, 95, 1271 (1995); Ungerer et al., *Circulation*, 87, 454, (1993)).

In one embodiment, therapeutic cells are cardiomycytes, e.g., prepared from cardiac tissue or noncardiac tissue. Detection of expression of cardiomyocyte-specific proteins may be accomplished using antibodies to, for example, myosin heavy chain monoclonal antibody, e.g., MF 20 (MF20), sarcoplasmic reticulum calcium ATPase (SERCA1), e.g., mnAb 10D1, or gap junctions, e.g., using antibodies to connexin 43, as well as phospholamban, or by detecting the expression of the following genes: titin (Z-band), α-actinin, myomesin, sarcomeric myosin heavy chain, sarcomeric α-actin, cardiac tropinin T, M protein, RyR2, Cx40 and Cx 43. For the differentiation of ES cells to cardiomyocytes, the expression of the following genes may be monitored: Nkx 2.5, MEF2c, GATA 4/5/6, desmin, M-cadherin, beta1-integrin, oxytocin, oxytocin receptor, cardiac myosin heavy chain, myosin light chain 2A or 2C, cardiac tropinin I, troponin C and ANP. For the differentiation of bone marrow derived MSCs, the expression of the following genes may be monitored: beta1 and beta2 adrenergic receptors, e.g., via the response of cells to isoproterenol, or muscarinic receptors, e.g., via the response of cells to carbachol.

Atrial-like cells may be identified as cells having ion currents associated with muscarinic acetylcholine-activated $K^+$ channels and inwardly rectifying $K^+$ channels, but not hyperpolarization-activated pacemaker channels, while ventricular-like cells may be identified as cells having ion currents associated with inwardly rectifying $K^+$ channels and SR ryanodine-sensitive calcium-release channels but not muscarinic acetylcholine-activated $K^+$ channels or hyperpolarization-activated pacemaker channels. Sinus node-like cells may be identified as cells having ion currents associated with muscarinic acetylcholine-activated $K^+$ channels and SR ryanodine-sensitive calcium release channels, and hyperpolarization-activated pacemaker channels but not inwardly rectifying $K^+$ channels.

3. Chemical Conditioning

Figure 2A:
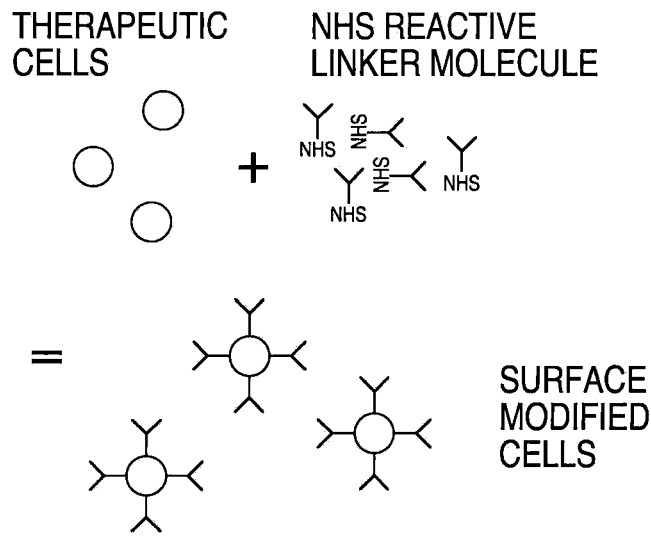
FIG. 2A illustrates surface modified therapeutic cells.
Figure 2B:
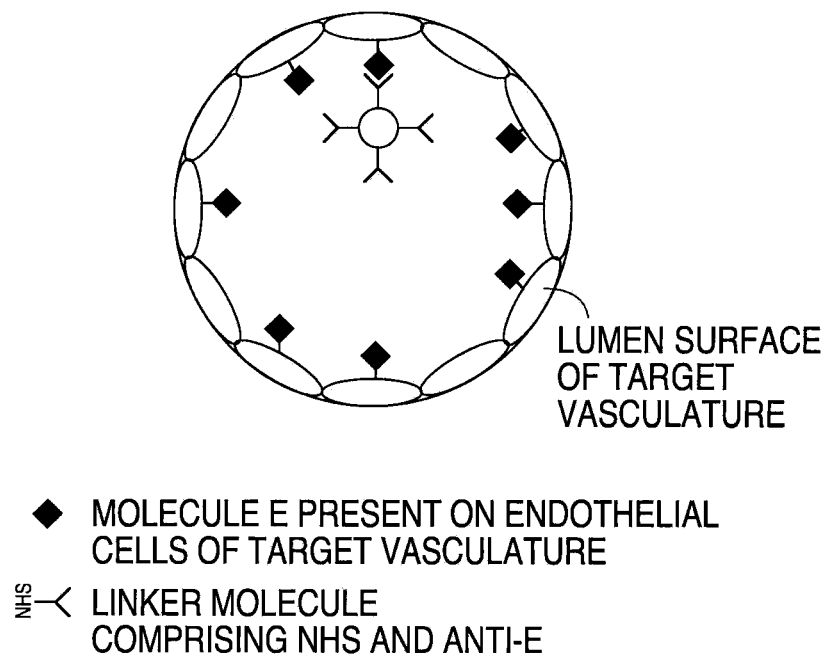
FIG. 2B illustrates a therapeutic cell attached to a lumen surface by an N-hydroxy succinimide (NHS) reactive linker molecules.

In another embodiment, molecules or molecular moieties possessing affinity to the luminal surface of the target area vasculature are chemically conjugated to the surface of a therapeutic cell using methods known to the art, as illustrated in FIGS. 2A and 2B. FIG. 2A illustrates surface modification of therapeutic cells using NHS reactive linker molecules. In the figure, the NHS linker molecules each include NHS and anti-E. FIG. 2B illustrates a therapeutic cell attached to an endothelial cell of the target vasculature. The molecule or molecular moiety may be conjugated to the cell surface via a spacer molecule to enhance accessibility. One such molecule may possess more than one molecular moiety with affinity to the target surface. In certain embodiments, the spacer may be branched. Attachment molecules may be chemically conjugated, i) to amine groups using reactive esters, epoxide, aldehydes, ii) to sulfhydryl groups using maleimides, vinyl sulfones, iii) to carboxyl groups using dimethylaminopropyl-carbodiimide (EDC) chemistry, iv) or non-selectively using photochemistry.

For example, the surface of the therapeutic cell, e.g., a stem cell, may be modified to display or express an antibody to a receptor present on an endothelial cell of the target vasculature, e.g., E-Selectin, PECAM (CD31), and the like. In addition to the biological conditioning methodology as described herein, the therapeutic cell may be modified by chemically conjugating a vinyl sulfone (VS)-PEG-antibody molecule to sulfhydril groups to the cell surface. To generate a VS-PEG-antibody molecular construct, a cysteine residue may be inserted in the C terminus of the antibody or antibody fragment by using genetic engineering methodologies. The genetic code of an antibody of interest may be obtained, for example, from clonal selection through phage display. The genetic code of a monoclonal antibody may be modified to include a cysteine residue at the C terminus and expressed in a bacterial or mammalian expression system (Härmä et al., *Clinical Chemistry*, 46:1755-1761 (2000)). These engineered antibodies may be incubated with a molar excess of VS-PEG-VS to yield the above sulfhydril-reactive VS-PEG-antibody.

Alternatively, antibodies may be attached to a therapeutic cell surface through a linking bridge, e.g., a biotin-avidin bridge. For this purpose, NHS-PEG-biotin is conjugated to the cells by incubating cells with the NHS-PEG-biotin. Subsequently, cells are incubated with avidin, or derivatives thereof such as streptavidin, NeutrAvidin and the like. As avidin provides four opposing (two on each side) binding pockets for biotin, the cell surface will present two empty avidin pockets on its surface. In a final step, biotinylated antibodies are attached to the cell surface by incubation of the biotinylated antibody with cells presenting avidin at their surface As above, other antibodies, fragments thereof, or molecules other than antibodies may be conjugated to the surface of a therapeutic cell.

Molecules or molecular moieties possessing affinity to the luminal surface of the target area vasculature may be introduced into and anchored in the membrane of a therapeutic cell by liposomal or micelle delivery.

For example, CD31 antibodies or fragments thereof may be conjugated to a phosphatidyl ethanolamine lipid with di-C16 or longer chains. The lipid anchor may than be introduced into the cell membrane through micelle or liposomal fusion. Alternatively, hydrophobic peptide alpha-helices (such as poly-leucine), short or hydrophobic polymer chains may serve as membrane anchors.

As above, other antibodies, fragments thereof, or molecules other than antibodies, e.g., affibodies, may be anchored in the membrane of the therapeutic cells. For molecules with an inherent transmembrane-domain, modification may not be necessary.

Proteins and peptides are amino acid polymers containing a number of reactive side chains. In addition to, or as an alternative to, these intrinsic reactive groups, specific reactive moieties can be introduced into a polymer chain by chemical modification. These groups, whether or not they are naturally a part of the protein or are artificially introduced, serve as "handles" for attaching a wide variety of molecules, including other proteins. The intrinsic reactive groups of proteins are described in the following section.

(a) Amines (Lysines, α-Amino Groups).

One of the most common reactive groups of proteins is the aliphatic s-amine of the amino acid lysine. Lysines are usually present to some extent and are often quite abundant. Lysine amines are nucleophiles above pH 8.0 ($pK_a$=9.18) and therefore react with a variety of reagents to form stable bonds. Other reactive amines that are found in proteins are the α-amino groups of the N-terminal amino acids. The α-amino groups are less basic than lysines, are reactive at around pH 7.0, and can be selectively modified in the presence of lysines.

(b) Thiols (Cystine, Cysteine, Methionine).

Another common reactive group in proteins is the thiol residue from the sulfur-containing amino acid cysteine and its reduction product cysteine (of half-cystine), which are counted together as one of the 20 amino acids. Cysteine contains a free thiol group, which is more nucleophilic than amines and is generally the most reactive functional group in a protein. It reacts with some of the same modification reagents as do the amines discussed in the previous section and in addition can react with reagents that are not very reactive towards amines. Thiols, unlike most amines, are reactive at neutral pH, and therefore they can be coupled to other molecules selectively in the presence of amines. This selectivity makes the thiol group the linker of choice for coupling two proteins together, since methods that only couple amines (e.g., glutaraldehyde, dimethyladipimidate coupling) can result in formation of homodimers, oligomers, and other unwanted products. Since free sulfhydryl groups are relatively reactive, proteins with these groups often exist in their oxidized form as disulfide-linked oligomers or have internally bridged disulfide groups. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) is required to generate the reactive free thiol. In addition to cystine and cysteine, some proteins also have the amino acid methionine, which contains sulfur in a thioether linkage. When cysteine is absent, methionine can sometimes react with thiol-reactive reagents such as iodoacetamides.

(c) Phenios (Tyrosine).

The phenolic substituent of the amino acid tyrosine can react in two ways. The phenolic hydroxyl group can form esters and ether bonds, and the aromatic ring can undergo nitration or coupling reactions with reagents such as diazonium salts at the position adjacent to the hydroxyl group. Tyrosyl residues can react with diazonium compounds. For example, a p-aminobenzoyl biocytin derivative has been diazotized and reacted with protein tyrosine groups.

(d) Carboxylic Acids (Aspartic Acid, Glutamic Acid).

Proteins contain carboxylic acid groups at the carboxy-terminal position and within the side chains of the dicarboxylic amino acids aspartic acid and glutamic acid. The low reactivity of carboxylic acids in water usually makes it difficult to use these groups to selectively modify proteins and other biopolymers. In the cases where this is done, the carboxylic acid group is usually converted to a reactive ester by use of a water-soluble carbodiimide and then reacted with a nucleophilic reagent such as an amine or a hydrazide. The amine reagent should be weakly basic in order to react specifically with the activated carboxylic acid in the presence of the other amines on the protein. This is because protein cross-linking can occur when the pH is raised to above 8.0, the range where the protein amines are partially unprotonated and reactive. For this reason, hydrazides, which are weakly basic, are useful in coupling reactions with a carboxylic acid. This reaction can also be used effectively to modify the carboxy terminal group of small peptides.

(e) Other Amino Acid Side Chains (Arginine, Histidine, Tryptophan).

The chemical modification of other amino acid side chains in proteins has not been extensive, compared to the groups discussed above. The high $pK_a$ of the guanidine functional group of arginine ($pK_a$=12-13) necessitates more drastic reaction conditions than most proteins can survive. Arginine modification has been accomplished primarily with glyoxals and α-diketone reagents. Tryptophan modification requires harsh conditions and is seldom carried out except as a method of analysis in structural or activity studies. Histidines have been subjected to photooxidation and reaction with iodoacetates.

(f) Non-Specific Attachment.

Photoreactive chemistry may be used to attach molecules to the cell surface in a non-specific way. When activated by UV or visible radiation, photoreactive groups react with carbohydrates, proteins or lipids present at the cell membrane interface. Examples for photoreactive moieties include but are not limited to phenyl azides, nitrophenyl azides, hydroxyphenyl azides.

(g) Other Methods.

In another embodiment, irritants and/or stimulants may be mixed with therapeutic cells immediately before infusion.

As discussed herein, the surface of a therapeutic cell is modified to enhance engraftment of the cell at a target vasculature site or region. In one embodiment, "receptor-ligand" interaction is exploited to enhance engraftment. For example, the HCELL adhesion molecule present on a therapeutic cells interacts with E-Selectin present on an endothelial cell at the target site, PSGL interacts with P-Selectin, and VLA-4 interacts with VCAM-1 and/or ICAM-1. Thus, the upregulation of any of these adhesion molecules, or the introduction of any of these adhesion molecules onto the respective cell membranes, by any methodology as discussed herein, will increase the membrane concentration of these molecules and therefore, increase the affinity between the therapeutic cell and target cell. In one embodiment, either the expression, display, or both of HCELL, E-Selectin or both is either upregulated, increased, or both, because of E-Selectin's involvement in the initial recruitment and initiation of rolling adhesion.

In another embodiment, any combination of the methods discussed herein may be used to enhance engraftment of a therapeutic cell to a target cell For example, the expression of CD34 on a stem cell can be upregulated by the genetic methods discussed herein, and then subsequently modified with a bi-functional linker molecule as discussed to enhance engraftment of the stem cell at target endothelium.

D. Delivery and Infusion Regimes of To Enhance Engraftment of Therapeutic Cells

As disclosed herein, the present subject matter is directed to an apparatus and method to enhance the engraftment of therapeutic cells at a target site in vasculature. To increase therapeutic cell attachment at the target site, therapeutic cells can be conditioned mechanically to upregulate the expression of adhesion molecules. In another embodiment, the engraftment of therapeutic cells at the site of target vasculature is enhanced by regulating the hemodynamics of the delivered therapeutic cell solution to establish flow dynamics conducive to therapeutic cell/target site interaction. For example, therapeutic cell residency time at the target site can be increased by increasing the viscosity of the therapeutic cell solution to reduce the flow rate of the cell solution, by impeding the flow proximally by employing flow resistance, or by proximal occlusion, which allows for control of the flow rate of the infused cell suspension.

1. Exemplary Protocols for Shear-Induced Modification of Cell Surface

Numerous cell types are known to be activated by shear at shear stress rates above 120 dynes/cm2 (Moritz et al., *Thrombosis Research*, 22:445-455 (1981)). In one embodiment, therapeutic cells are loaded into a catheter. With the tip of a catheter immersed in the cell suspension, a syringe pump is programmed to perform 1-3 inject/withdraw cycles at high shear rates of, for example, 80 dynes/cm$^2$ and above.

Suitable syringe pumps for use in the present invention include commercially available syringe pumps such as bench top models (New Era Pump Systems, Inc., Farmingdale, N.Y., USA, www.syringepump.com; Ted Pella, Inc., Redding, Calif., USA, www.tedpella.com). U.S. Pat. No. 5,342,298 discloses a programmable pump to deliver cells through an infusion catheter into myocardium. The cells in the catheter will then be activated, and, as discussed herein, adhesion molecules will be upregulated and expressed. Once the cells are delivered into the target vasculature, they will be able to more quickly adhere to target vasculature and extravasate into the surrounding myocardium.

In an alternative embodiment, therapeutic cells are shear activated before loading into a catheter, for example, by controlled shaking or agitation in a table-top device.

In another embodiment, the inject/withdraw cycles may be performed with the catheter already positioned at the delivery site and with occlusion balloon on. In this case, the shear cycle may not only activate the therapeutic cells that are in the delivery system, but may also upregulate adhesion molecules on the endothelial cells lining. This will allow better adhesion of the delivered cells, e.g., bone marrow mononuclear fraction, to the vasculature that contains endothelial cells.

In yet another embodiment, the inject/withdraw cycle may be performed with the catheter positioned at the delivery site and with occlusion balloon on. Shear activation is performed with a saline flush to activate target endothelial cells only. The therapeutic cells are then delivered to the target vasculature post saline flush.

In one embodiment, the shear rate targets are defined for each individual cycle. Shear rate is a function of length of the catheter lumen in which cells are residing, as well as the diameter of such catheter, and fluid velocity produced by the syringe. The following formula may be used:

$$\text{Tau(shear stress)} = -mu(dv/dr) \text{ and } \text{Tau} = (\text{del } P/2L)r$$

With these two equations, sheer stress one can solve for (Tau) using known device (R, L), pump (Del P and DV/dr), and fluid (mu) parameters. [Tau=Fluid Shear Stress; mu=Fluid Viscosity; V=Fluid Velocity (which may be selected on a syringe pump, and is function of the syringe size); r=Radial Distance (distance from the center of the circular cross-section or inner lumen radium); P=pressure generated by the pump and L is length of the tube]. Bird et al., *Transport Phenomena* (1960).

2. Protocols to Induce Proximal Flow Impedance

The residence time of therapeutic cells, i.e., the duration of time the therapeutic cells are in the vicinity of the target site or area, can be increased to enhance retention at target site by controlling hemodynamics, for example, by reducing the flow rate in the target area vasculature. The flow rate can be controlled using a proximal flow impedance device. Exemplary impedance devices include a partially inflated balloon, a doughnut-shaped balloon (having a middle opening that provides reduced blood flow rate), a balloon with longitudinal channels in the surface, a spiral balloon (having profusions at the time of some delivery and wherein the flow is reduced by forcing migration between adjacent spirals) or a balloon having fluid flow constrictions. In one example, flow can be temporarily stopped by complete flow occlusion immediately after infusion of therapeutic cells and at a time when approximately a large number of therapeutic cells are located within the target area.

In another example, a proximal flow impedance device is introduced to induce ischemia. According to one example, the blood flow is not entirely occluded but rather, merely reduced to some non-zero flow rate. The non-zero flow rate allows infusion of therapeutic cells. In one example, the flow is reduced from an initial flow rate by a factor of 10 to 70 percent. Typically, an arterial occlusion is considered clinically relevant or flow limiting when the occlusion is approximately 70% or greater. Accordingly, the level of occlusion provided by a flow resistor of the present subject matter will by approximately 70-100% of normal vessel diameter. As noted, exemplary flow resistors include a balloon having longitudinal grooves along the perimeter through which fluid flows or a doughnut-shaped balloon in a manner similar to a vessel lesion.

In one example, the residence time is increased by changing the hemodynamics of the therapeutic cells. The hemodynamics can be tailored by increasing the viscosity of the solution causing the solution to flow more slowly. Increasing the viscosity serves to impede the flow proximal to the target site. In addition, flow proximal to the target site can be reduced by adding a flow resistance.

Other kinds of flow resistors are also contemplated, including, for example, an insertion device fabricated of porous or sintered material.

3. Delivery of Viscous Agents to Enhance Engraftment of Therapeutic Cells

Once delivered to the capillary bed, a therapeutic cell contacts a cell at the target site, e.g., an endothelial cell. If engaging the endothelial cell through focal molecular adhesion (receptor to ligand binding), the therapeutic cell rolls along the endothelial surface until it either breaks free or adheres firmly. An example for such rolling interaction is the rolling of leucocytes along endothelial cells. Rolling speeds are on the order of 40-60 microns/sec, (Ramos, C. et al., *Circ Res.*, 84: 1237-1244 (1999); Prorock, A. et al., *Am J Physiol Heart Circ Physiol.*, 284: H133-H140 (2003); Baudry, N. et al., *Am J Respir Crit Care Med*, 158: 477-483 (1998)) which translates into a contact time between a rolling cell and a given endothelial cell of roughly 0.5 seconds.

To increase the probability of a therapeutic cell contacting a target cell, in one embodiment, viscous agents are delivered with the therapeutic cells to a subject. Factors that effect blood viscosity include plasma viscosity, aggregation of red blood cells, internal viscosity of red cells, hemoconcentration, aggregation of platelets and concentration of white cells. Flow velocity is inversely proportional to viscosity. Higher viscosity leads to a reduced rate of flow, which in turn increases the residence time of the therapeutic cells at the target site, thus increasing the time in which the therapeutic cells have to engraft, i.e., adhere and transmigrate into the target site, e.g., an infarcted region.

For example, adding a sufficient amount (about 0.25%-5% by weight) of a higher viscosity biobeneficial/biocompatible medium such as tocopherol (Vitamin E), lipid emulsions such as emulsified vegetable oil, surfactant (Cremaphor), or a hydrophilic polymer increases the viscosity of the plasma or the therapeutic cell injection medium, thus increasing the time of residence of therapeutic cells at the target site during cell delivery. Examples of suitable hydrophilic polymers are PEG, PVA (Polyvinyl alcohol), PVP (polyvinylpyrrolidone), Dextran, and dextran sulfate. Molecular weights of the dissolved hydrophilic polymers can range up to 200K Daltons, and in one embodiment are between 5K to 30K Daltons. These higher viscosity biobeneficial/biocompatible media increase the viscosity of plasma, thus increasing the time of residence of therapeutic cells at the target site during cell delivery.

Alternatively, to increase the residency time of the therapeutic cell at a target location, the therapeutic cell is contacted with, e.g., incubated with, activated platelets or platelet-derived microparticles to cause the formation of clumps or rosettes. (Janowska-Wieczorek et al., Blood, 98:3143-3149 (2001)). After filtering/controlling the clump size, a composition containing well controlled therapeutic cell clumps leads to embolization in the capillaries, which increases the dwell time of the cells in the capillaries as well as provides a transient ischemic episode that upregulates adhesion and homing molecules in the surrounding interstitial space. Thus, an efficient transport of therapeutic cells to the target site is provided.

In other embodiments, an engraftment enhancing agent such as a calcium ionophore, oleic acid, histamine, DMSO, histamine, bradykinin, serotonin, thrombin, VEGF, a leukotriene such as LTC4, LTD4, LTE4, or a vasodilator, such as an ACE inhibitor or a nitrate, are added to the injectate to open the interstitial spaces and/or increase vascular wall permeability for more effective cell delivery (Rutledge et al., *Circulation Research,* 66: 486-495 (1990); Saxena et al., *J. Clin. Invest.,* 89: 373-380 (1992); Gupta et al., *J. Leukoc Biol.,* 70(3): 431-438 (2001); and van Nieuw Amerongen et al., *Circ. Res.,* 83:1115-1123 (1998)). Liu et al., *Am. J. Hematol.,* 74: 216-217 (2003) reported that adhesion molecules were dramatically increased on CD34+ cells surface in the presence of platelet microparticles, and these cells were shown to adhere better on endothelial cells and fibronectin.

In an alternative embodiment, therapeutic cells, e.g., stem cells, are delivered in a two-phase process via the capillaries leading to the target site, e.g., myocardial tissue of the heart, by means of the delivery device described herein. Phase One (1) includes the use of a high viscosity "foam" that contains $CO_2$ and an engraftment enhancing agent such as a cytokine, e.g., oxidized LDL, tumor necrosis factor-alpha, interleukin-1 and other cytokines that stimulate the expression of cell adhesion molecules on the surfaces of cells, and/or a chemokines, such as IL-8, SDF-1, MIP-1, MCP-1/2/3/4 and lymphoactin. In addition, a device such as the one disclosed in Gordilo et al., *Physics of Fluids,* 16: 2828 (2004) can be used to generate the $CO_2$ microbubbles.

In another embodiment, the "foam" includes ultrasonic contrast agents and $CO_2$ microbubbles. Several cardiac and intravenously injectable vascular ultrasound contrast agents are commercially available, such as Albunex (Molecular Biosystems), Optison (Molecular Biosystems), Echovist (Schering), Levovist (Schering), EchoGen (Sonus Pharmaceuticals), Definity (Du Pont Merck), Imagent (Alliance Pharmaceutical), Sonazoid (Nycomed-Amersham), SonoVue (Bracco Diagnostics), Quantison (Quadrant), Biosphere (Ponit Biomedical), and AI-700 (Acusphere).

The physical nature of the solution results from the use of a mixing device, for example, associated with the delivery device. The $CO_2$ microbubbles promote tissue ischemia (necessary ischemic preconditioning) by elevating the concentration of carbon dioxide in the blood. This elevation decreases the concentration gradient for carbon dioxide between the cardiac cells and the blood resulting in a decreased diffusion of carbon dioxide out of the cardiac cells and an elevated carbon dioxide level inside the cells. The elevated carbon dioxide level induces an ischemic state with an decrease tissue pH (acidosis). The engraftment enhancing agent induces a firm adhesion of the therapeutic cells to the capillary walls once the cells are introduced in Phase Two (2). Phase Two optionally includes the application of high viscosity "foam" containing $CO_2$ and therapeutic cells mixed together. By "foam" is meant a collection of $CO_2$ microbubbles of sufficient size to increase blood viscosity and slow the movement of blood and the cells therein as they pass through capillaries and venules. Both the premixed engraftment enhancing agent solution and the premixed therapeutic cell solution are relatively high in viscosity, compared to blood viscosity. The viscous nature of the foam combined with the microbubbles of $CO_2$ would allow the therapeutic cells to remain in the particular area for a predetermined period of time. Once the $CO_2$ is absorbed, the foam dissipates, resuming normal blood flow through the myocardia.

In one embodiment, an additional agent is delivered via the device to neutralize the foam.

4. Delivery of Agents to Increase 'Bumping' Frequency

The probability of a therapeutic cell successfully engrafting at a target site increases if platelets are added to cause more bumping of the cells against the vessel surface. The process of cell extravasation from the vessel wall into the myocardium involves the upregulation of adhesion molecules on the cell surface, as well as on the surface of the vessel's endothelium layer, and the ability of a therapeutic cell to interact with the endothelium. Thus, in order to initiate cell/surface contact, a therapeutic cell must first "bump" into the adherent surface, then roll along the surface at a velocity slow enough to allow adhesion molecules present on the therapeutic cell to contact, e.g., bind, with a corresponding adhesion molecules present on the target cell. The frequency of "bumping" dictates the number of therapeutic cells that will adhere to the endothelium and extravasate. For example, it has been reported that leukocytes in close proximity to endothelial cells upon entry into postcapillary venules experience frequent collisions with erythrocytes, which pushes the cells towards the vessel wall (Stein et al., *The Journal of Experimental Medicine,* 189: 37-39 (1999)).

In one embodiment, microbubbles with sizes equivalent to red blood cells are administered together with the therapeutic cell solution to increase the collision frequency potential, which optimizes the chance of cellular adhesion. In one embodiment, the microbubbles are about 10 microns in diameter, and are composed of a lipid such as phospatidyl choline, albumin, a degradable polymer such as polycaprolactone, PLGA poly(lactide-co-glycolide), Polyester-amide, polyphosphazine, tyrosine carbonate, and the like, or any combination thereof. The addition of microbubbles to the therapeutic cell solution increases the apparent viscosity of the fluid, which slows down the rolling of the therapeutic cells. In another embodiment, the microbubbles serve as a carrier of a substance, such as oxygen or NO to either induce a transient, local ischemic environment or to provide more oxygenation in the event of prolonged ischemia.

In another embodiment, platelet-derived microparticles (PMPs) are employed to increase bumping frequency. PMPs are released upon activation of platelets and express functional adhesion receptors, including $\alpha IIb\beta 3$ (CD41), P-selectin (CD62P), and other platelet membrane receptors such as CXCR4 and PAR-1 (Janowska-Wieczorek et al., *Blood*, 98:3143-3149 (2001)). PMPs released by activated platelets bind to membranes of therapeutic cells, e.g., CD34$^+$ therapeutic cells, and increase their adhesion to endothelial cells (Id.). PMPs can be prepared using methods known to the art. For example, PMPs can be collected from blood by centrifugation. Briefly, blood is centrifuged in order to collect platelet-rich plasma. Platelet rich plasma is then centrifuged in order to obtain platelet poor plasma. The platelet poor plasma is then centrifuged to collect the platelet microparticles (PMPs). In one embodiment, PMPs are collected from aged blood. See, for example, Forlow et al., *Blood*, 95: 1317-1323 (2000); Janowska-Wieczorek et al., *Blood*, 98: 3143-3149 (2001).

Bumping frequency can also be increased by employing liposomes, lipid vesicles or vesicles with membranes formed from di-block or tri-block co-polymers that can increase the viscosity of the medium and bumping frequency of the therapeutic cells with the endothelium when added to the delivery medium. The liposomes, lipid vesicles or vesicles with membranes formed from di-block or tri-block co-polymers have a size of approximately 100 nm-20 µm diameter, for example, approximately 100 nm-1 µm diameter. In one embodiment, the co-polymers have a size approximately 3-15 µm. In one embodiment, the liposome includes a therapeutic agent.

In yet another embodiment, microspheres are employed to increase bumping frequency. The microspheres may be composed of degradable polymers such as polycaprolactone, PLGA poly(lactide-co-glycolide), Polyester-amide, polyphosphazine, tyrosine carbonate, etc., or Alginate crosslinked with divalent Ca, Ba or Sr cations. Microspheres may also be made of an extra-cellular matrix protein such as collagen or gelatin, crosslinked with glutaraldehyde to prevent quick dissolution.

5. Delivery of Agents to Enhance Homing of Therapeutic Cells to Target Vasculature Stem cells are precursor cells capable of proliferation, self-renewal, and differentiation into specialized tissues and organs, including cardiomyocytes. The repopulation of cardiomyocytes to regenerate new myocardium can mitigate the remodeling process. The "homing process" involves stem cell migration to the sites of injury or ischemia, which provides an environment that is favorable to growth and function. This microenvironment is a stimulus for homing and differentiation of stem cells of the appropriate lineage. It increases vascular permeability and expression of adhesion proteins like integrin, along with homing receptors that facilitate their attachment, which is mediated by cell-to-cell contact and chemoattractant release from local tissue injury.

In one embodiment, chemokines, a superfamily of small proteins that function as potent chemotactic agents, some of which have a tissue- and inflammation-specific distribution, and others which are widely distributed, are exploited to attract the therapeutic cells to the target vascular endothelium. For example, SDF-1 plays a role in homing (Sackstein, *J. Invest. Dermatol.*, 122: 1061-1069 (2004)). SDF-1 is infused into the target vasculature before infusion of therapeutic cells to provide a homing stimulus. Alternatively, SDF-1 is contacted with therapeutic cells prior to infusion, which contact initiates homing signaling pathways leading to increased retention of therapeutic cells upon infusion into the target vasculature.

Alternatively, it has been shown that exposure of cell to cytokines alters expression patterns of these cells. Therefore, infusion of platelet derived cytokines/growth factors, VEGF, FGF, prior to infusion of therapeutic cells may increase cell retention at target vasculature.

Cytokines, such as granulocyte colony-stimulating factor (G-CSF) and stem cell factor (SCF), increase bone marrow stem cell mobilization, homing, and engraftment to infarcted myocardium. The endogenous repair process after myocardial necrosis can also be enhanced with specific growth factors, such as insulin-like and hepatocyte growth factors, that stimulate cardiomyocyte replication and attract cardiac resident stem cells.

The migratory capacity of transplanted progenitor cells might be dependent on natural growth factors such as vascular endothelial growth factor (VEGF) and stromal cell-derived factor-1 (SDF-1). The expression of VEGF and SDF-1 is highly up-regulated in hypoxic tissue, supporting the hypothesis that these factors may represent homing signals crucial to the recruitment of circulating progenitor cells to assist the endogenous repair mechanisms in the infarcted tissue.

Transplanted stem cells must engraft and proliferate efficiently after myocardial infarction to derive a maximal clinical benefit. With a smooth transition process, newly formed cardiomyocytes are required to be connected intercellularly through electrical coupling with other cardiomyocytes and the formation of connexin, an integral membrane protein constituent of gap junctions. Paramount to the survival of the stem cells is simultaneous neovascularization to keep up with the metabolic requirements of the newly transplanted cells to perform contractile work.

As described herein, mediators of stem cell mobilization, migration and attachment include granulocyte colony-stimulating factor, stem cell factor, vascular endothelial growth factor (VEGF) and stromal cell-derived factor-1 (SDF-1).

In another embodiment, magnetically targeted therapy is used to manipulate the homing process. Therapeutic cells, such as stem and progenitor cells including hematopoeitic progenitor (CD34$^+$) and mesenchymal stem cells (MSCs), take up and incorporate into perinuclear endosomes micronscale iron oxide particles without affecting cell proliferation or functional capabilities (Hinds et al., *Hematopoiesis*, 102: 867-872 (2003)). Therapeutic cells are contacted with such particles, which are either attached to the cell or taken up by the cell, and delivered to a subject. As described herein, application of a magnetic field gradient following delivery of the therapeutic cells and magnetic carriers enhances engraftment of therapeutic cells to the target vasculature (see in general Pankhurst et al., *J. Phys. D: Appl. Phys.*, 36: R167-R181 (2003)). Suitable magnetic particles are known to the art, and include super-paramagnetic nanoparticles with iron oxide. Additional examples of suitable particles are shown in Tables 1 and 2.

TABLE 1

| Name | Diameter (μm) | Polymer composition/surface modification | End groups and activation possibility | Immobilized antibodies | Other immobilized compounds | Manufacturer/supplier |
|---|---|---|---|---|---|---|
| BioMag | ~1 | Silanization of iron oxides | —COOH, —NH$_2$ | Secondary Abs, anti-CD Abs, anti-fluorescein Ab | Protein A, protein G, streptavidin, biotin | PerSeptive Biosystems, Farmingham, MA, U.S.A. |
| Dynabeads M-280 | 2.8 | Polystyrene | Tosyl-activated | Secondary Abs, anti-CD Abs, Abs against *E. coli* O157, *Salmonella Listeria*, *Cryptosporidivan* | Streptavidin, oligo (dT) | Dynal, Oslo, Norway |
| Dynabeads M-450 | 4.5 | | | | | |
| Dynabeads M-500 | 5 | | | | | |
| Estapor | ~1 | Polystyrene | —COOH, —NH$_2$ | | | Prolabo, Fontenay-sous-Bois, France |
| Iobeads | ~1 | | | Anti-CD Abs, secondary Abs | Avidin | Immunotech, Marseille, France |
| M 100 | 1-10 | Cellulose | —OH | | | Scigen, Sittingbourne, U.K. |
| M 104 | | | | | | |
| M 108 | | | | | | |
| MagaBeads | 3.2 | Polystyrene | —COOH, —NH$_2$, epoxy | Secondary Abs | Streptavidin protein A, protein G | Cortex Biochem., San Leandro, CA, U.S.A. |
| Magne-Sphere | <1 | | | | Streptavidin | Promega, Madison, WI, U.S.A. |
| Magnetic beads | 0.8 | Latex | | | Streptavidin, protein A, protein G | ProZyme, San Leandro, CA, U.S.A. |
| Magnetic microparticles | 1-2 | Polystyrene | —COOH—NH$_2$ | | Protein A | Polysciences, Warrington, PA, U.S.A. |
| Magnetic particles | 1 | Polystyrene | | Anti-digoxigenin Ab | Streptavidin | Boehringer, Mannheim, Germany |
| Magnetic particles | ~1 | Polystyrene | | | | Bangs Labs, Fishers, IN, U.S.A. |
| MPG | 5 | Porous glass | —NH$_2$, hydrazide, glyceryl | | Streptavidin, avidin | CPT, Lincoln Park, NJ, U.S.A. |
| Sera-Mag | 1 | Polystyrene | —COOH | | Streptavidin | Seradyn, Indianapolis, IN, U.S.A. |
| SPHERO magnetic particles | Various (1-4.5) | Polystyrene | —COOH, —NH$_2$ | Secondary Abs | Streptavidin, biotin | Spherotech, Libertyville, IL, U.S.A. |
| XM200 microsphere | 3.5 | Polystyrene | —COOH | Secondary Abs | Protein A | Advanced Biotechnologies, Epsom, U.K. |

TABLE 2

| Name | Diameter (nm) | Polymer composition | End groups and activation possibility | Immobilized antibodies | Other immobilized compounds | Manufacturer/supplier |
|---|---|---|---|---|---|---|
| Ferrofluids | 135, 175 | Modified hydrophilic protein | —COOH, —NH$_2$ | Secondary Abs | Streptavidin, protein A | Immunicon, Huntingdon Valley, PA, U.SA. |
| MACS microbeads | 50 | Dextran | —OH | Secondary Abs, anti-CD Abs | Streptavidin, biotin | Miltenyi Biotec, Bergisch Gladbach, Germany |
| Magnetic nanoparticles | 90-600 | Starch, dextran, chitosan | —OH, —COOH | | Streptavidin, protein A, biotin | Micro-caps, Rostock, Germany |
| MagNIM | 50, 250, 500 | | —COOH, —NH$_2$ | Secondary Abs, Ab against *E. coli* O157 | Streptavidin, protein A | Cardinal, Santa Fe, N.M., U.S.A. |

In one embodiment of this method, both therapeutic cells and the lumen surface of the target vasculature are modified to include magnetically responsive particles. Either the therapeutic cells or the target surface is modified with permanently magnetized particles, and the compliment is modified with permanently magnetized, ferromagnetic or super-paramagnetic or paramagnetic particles. Modifications may be accomplished by cellular uptake of magnetic particles, by attachment or chemical conjugation of magnetic particles to the surface of therapeutic cells/target area surface as described herein for attachment molecules, or by attachment of vesicles/liposomes/micelles containing magnetic particles.

The magnetic particles can range from about 10 nm to about 10 μm in diameter. In one embodiment, the diameter of the particle is about 10 nm to about 1 μm, and in another embodiment about 50 nm to about 500 nm. The particles may comprise rare earth magnetic material, ferrous components, and/or iron oxides.

The magnetic particles may be labeled with adhesion molecules, such as CD34, CD133, or antibodies thereof.

In one embodiment, a magnetically modified therapeutic cell is attracted into the target area by magnetic force generated through an external magnetic field gradient. In a magnetic field with a gradient, magnetized particles, or magnetically responsive particles (such as paramagnetic or superparamagnetic particles) are subject to a force in the direction of the gradient and proportional to the field gradient and the magnetic moment of the particle (in the case of paramagnetic particles, this moment is induced by the external field, and thus the attractive force also becomes a function of the magnetic field strength as well as the magnetic susceptibility of the particle). If, for example, the target vasculature is on the surface of the heart, and the target tissue is the local myocardium, then a magnetic field gradient directed perpendicular to the vascular wall and towards the target myocardium will exert a force directed towards the vessel wall along the target tissue on the magnetically responsive particles. As described above, cells may be magnetically modified by internalization of magnetic particles of attachment of such particles to the surface of the cells. This may be accomplished by using magnetic particles modified at their surface with antibodies to receptors present on the therapeutic (stem) cells. Such particles are commercially available.

Alternatively, magnetic particles may be introduced into the cell by magnetic cationic liposomes (MCLs). Magnetic cationic liposomes are liposomes with a membrane with cationic lipids and are filled with magnetically responsive nanoparticles. The electrostatic interaction between the cationic membrane and cell membranes results in internalization of the nanoparticles into the cell. In addition, magnetically labeled cells may be imaged by MRI, thereby allowing to assess amount of cells retained in the target area and as well as their spatial distribution.

E. Application of Magnetic Field Gradient Following Delivery of Therapeutic Cells Comprising Magnetic Nanoparticles A magnetic nanoparticle can be manipulated by an external magnetic field gradient (Pankhurst et al., *J. Phys. D: Appl. Phys.*, 36: R167-R181 (2003)).

In one example, the subject matter is directed to proactive retention of cells by a surface chemistry that increases the mutual affinity. The affinity of the cell to the surface of the target vasculature is increased or the system is modified to increase susceptibility to magnetic attraction forces. Such changes result in an increased dwell time, or residency, and increasing the stickiness. As such, the stickiness serves to retain or capture the therapeutic cells.

In one example, the therapeutic cells are combined with or infused with magnetic particles using different methods. Ferrous oxide has been demonstrated. The magnetic particles can be adhered to the therapeutic cells by various methods, including cellular uptake, attachment chemical conjugation, incubation and attachment of vesicles.

A magnetic field applied externally can be used to direct the cells to a target site. In various examples, either the endothelial cells, the therapeutic cells or both the endothelial cells and therapeutic cells are treated with the magnetic particles.

For example, with some mononuclear cells, magnetic particles of a particular size are ingested. Ingestion can be facilitated with electroproration, for example. Other commercially available tools, such as magnetic beads, are affixed using surface adhesion. In one example, the therapeutic cells are modified with a specific antibody.

The magnetic attraction forces can be used to enhance engraftment. For example, the therapeutic cell mixture is mixed with magnetic beads and then the beads attach specifically to the target cells and then those cells are retained by a magnetic force.

In the present subject matter, the magnetic force is used to draw therapeutic cells to a particular location on the target using a magnetic field gradient. For example, by establishing a magnetic field gradient directed perpendicular to the surface of the heart, followed by flushing the therapeutic cells, the cells will be directed to the vessel wall of the target vasculature.

Figure 3:
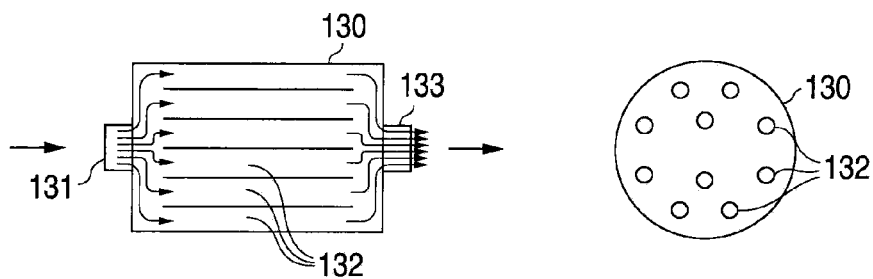
FIG. 3 illustrates an externally applied magnetic field gradient and an organ.
Figure 3:
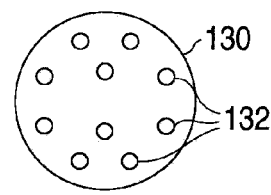
Figure 3:
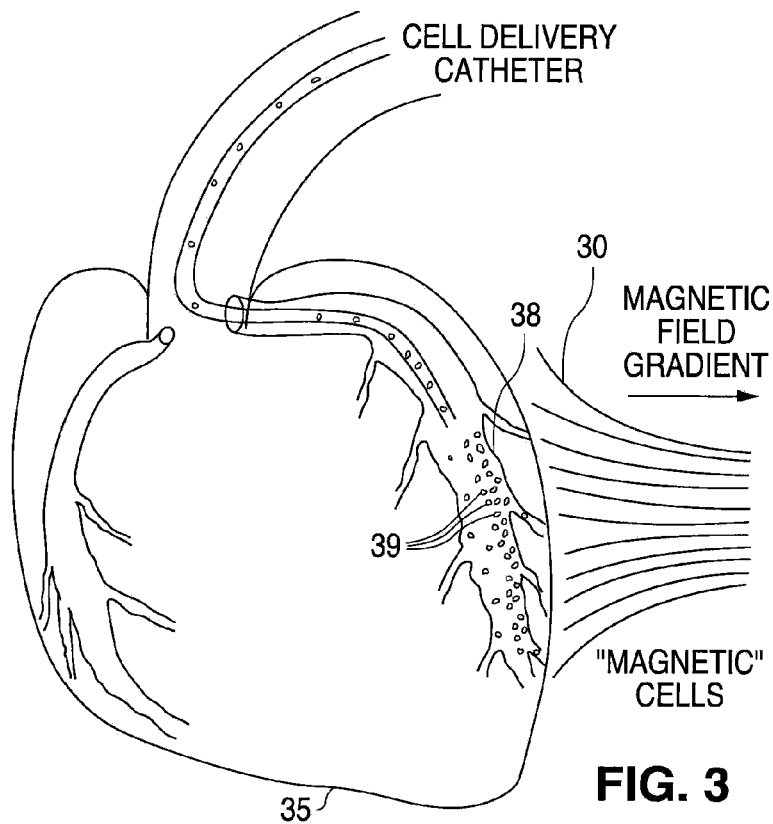

The magnetic gradient is applied perpendicular using a static magnetic field source. In one example, the field is applied externally through an MRI-like magnet or a strong magnet external to the body. In one example, the magnetic field is oriented such that the field gradient is normal to the surface of the heart in the target area. As such, the magnetic particles will experience a force normal to the surface of the heart. FIG. 3 illustrates organ 35 having damaged vessel 38. Static magnetic field gradient 30 is applied externally and exerts a magnetic force on magnetic particles 39 in a direction substantially normal to vessel 38. In the figure, magnetic particles 39 are attached to therapeutic cells.

The magnetic beads used to enhance engraftment of therapeutic cells are mixed, and optionally labeled. In one example, the beads are labeled to attach them to the cells. Examples of labels include an antibody to CD-34, or CD-133, or an activated bead that has surface chemistry that is amine-reactive.

The applied field generates a magnetic attraction that serves to slow the flow in the localized region at the target and also tends to increase the "adhesiveness" of a therapeutic cell to a target cell, which forces the therapeutic cells to dwell longer at the target location. In one embodiment, a magnetic field may be applied for the duration of the infusion and possible dwell time. Infusion duration times may vary anywhere from 30 seconds to 1 hour. Exposure to magnetic fields may be in similar time frame. For example, cells may be infused in 30 second increments, followed by 3 minute occlusion periods. After the therapeutic cells engage with the vessel wall, then the biological interaction and the interaction between the receptor occurs.

F. Compositions, Dosages and Routes of Administration of Therapeutic Cell Compositions Compositions comprise therapeutic cells, including cells from different sources, and optionally agents that enhance therapeutic cell engraftment, survival, proliferation and/or differentiation, enhance cardiac function or stimulate angiogenesis. The cells to be administered may be a population of individual cells or cells grown in culture so as to form a two dimensional or three dimensional structure. The number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered to, e.g., injected, the target region of interest, for instance, infarcted and tissue surrounding infarcted tissue. Agents which may enhance cardiac function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like. Such agents may optionally be present in the compositions or administered separately.

The cells are administered during a prophylactic, diagnostic or therapeutic vascular procedure or an invasive or minimally invasive surgical procedure. In one embodiment, the cells are administered post-myocardial infarction, within hours, e.g., 1 to 12 hours, to days, e.g., 1 to 2 days, and up to one or more weeks after myocardial infarction. Preferably, the administration of therapeutic cells is prior to scar formation. The cells may be administered intravenously, transvenously, intramyocardially or by any other convenient route, and delivered by a needle, catheter, e.g., a catheter which includes an injection needle or infusion port, or other suitable device. Some exemplary delivery apparatus and methods include, but are not limited to, the teachings provided herein.

In one embodiment, once administered, the therapeutic cells develop functional connections with adjacent cells, membrane channels with adjacent cells, including viable cells in the recipient, and, if not already differentiated, differentiate to myocardial cells.

Intracoronary catheter-based delivery of cells is known in the art. For example, the Transplantation of Progenitor Cells and Regeneration Enhancement in Acute Myocardial Infarction (TOP-CARE-AMI) pilot trial compared the effect of direct intracoronary infusion of autologous circulating progenitor cells and bone marrow cells in 20 patients who underwent primary angioplasty for acute myocardial infarction. In the study, cells were delivered via an over-the-wire balloon catheter advanced into a previously deployed stent.

III. Target Cells

To increase the probability and strength of attachment of therapeutic cells to cells located in the target site, i.e., target cells such as endothelial cells of the lumen surface of the target vasculature, the lumen surface may be modified such that the surface density of available adhesion molecules is altered, e.g., increased. As discussed herein, target cell adhesion molecules possess an affinity to the surface of the therapeutic cells, or molecular moieties thereof. Any of the methodology disclosed herein for the modification of a therapeutic cell might be used to modify a target cell as well. For example, target cells may be subjected to mechanical conditioning, biological conditioning, chemical conditioning, or any combination thereof. The expression of and/or number of endothelial adhesion molecules present on the surface of an endothelial cell such as ICAM-1, VLA-4 ligand (vascular cell adhesion molecule-1 (VCAM-1)) and E-selectin can be altered by these methods. Additional examples of adhesion molecules with an affinity to the surface of the therapeutic cells include antibodies to adhesion molecules present on the surface of therapeutic cells, e.g., anti-CD133 or anti-CD34 antibodies.

In one embodiment, the expression profiles of adhesion molecules on endothelial cells is manipulated by the magnitude and type of shear stress, i.e., laminar v. turbulent, and time of exposure to the shear stress. Any mechanism that induces shear stress might be utilized in the mechanical conditioning of target cells. For example, in one embodiment of mechanically conditioning target cells, a shear stress at rate of 20 dynes/cm$^2$ increases the expression of ICAM-1, and decreases VCAM-1 and E-selectin expression on target endothelial cells through modulation of transcriptional level gene expression (Chiu et al., *Arterioscel Thromb Vasc Biology*, 24:1-8 (2004)). In addition, shear influences NF-kB transcriptional factor in endothelial cells (Ganguli, A. et al., *Circ. Res.*, 96 (6): 626-634 (2005)). In another embodiment, saline fluid can be used to mechanically condition the target cells. In one example, the catheter is loaded with saline, saline is infused into the vessel, and through a cyclic infusion/withdraw regime using a pump connected to the distal end of the infusion catheter, shear is imposed onto endothelium of the targeted tissue.

As for "biological conditioning," target cells can be subjected to periods of hypoxia to upregulate adhesion molecules. For example, intercellular adhesion molecule (ICAM)-1 and vascular cell adhesion molecule (VCAM)-1 expression are upregulated in endothelial cells subjected to hypoxia (Ng et al., *Am. J. Physiol.*, 283: C93-C102 (2002)). In addition, hypoxia may directly activate NFk-B. NFk-B sites are present in the promoter of the ICAM-1 gene (Ohga et al., *Nippon Risho*, 58:1587-1591 (2000)). Therefore, hypoxia may directly activate the ICAM-1 through activation of NFk-B. Brief occlusions of target vasculature may also result in the upregulation of adhesion molecule expression on endothelial cells. In addition, target cells at a target site in the vasculature may be genetically modified using any method known to the art to upregulate expression of an adhesion molecules and/or to modify cell surface to enhance engraftment of therapeutic cells.

In addition, cells in the target area may be genetically modified prior to infusion of therapeutic cells to express (or increase the expression of) adhesion molecules or to increase the surface presentation of adhesion molecules. Genetic modification may be done by infusion of viral vectors, liposomal or micelle delivery vehicles, plasmids, as described herein. Intracoronary delivery of genetic material can result in transduction of approximately 30% of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., *Nat. Med.*, 6:1395 (2000)). The potential use of this approach for gene therapy for heart failure may be increased by the use of specific proteins that enhance myocardial uptake of vectors (e.g., cardiac troponin T). Improved methods of catheter-based gene delivery have been able to achieve almost complete transfection of the myocardium in vivo. Hajjar et al., (*Proc. Natl. Acad. Sci. USA*, 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Exemplary transgenes for delivery to a target cell include those genes that express corresponding adhesion molecules to those adhesion molecules found on a therapeutic cells, genes that express cytokines, genes that express Hypoxia Inducible Factor 1 (HIF-1), genes that express heat shock protein (HSP) (for cellular protection), cytokines (SCF, HGF), chemokines (SDF1), chemokine receptors (CXCRs, CCRs), proteolytic enzymes (MMP-2, MMP-9), angiogenic growth factors (VEGF receptors, such as VEGF-1/2/3/4; FGF receptors, such as FGFR-1/2/3/4), and anti-apoptosis (akt).

In one embodiment, a "two-step procedure" can be used to biologically modify a therapeutic cell and a target cell. For instance, cells at the target site can be modified, e.g. by delivery of a gene that would enhance expression of a counter-receptor; which modification is followed by the delivery of therapeutic cells. For example, on day 1, a gene of interest is delivered to a target site, and on day 2, therapeutic cells are infused. Thus, sufficient time for expression of the delivered gene is allowed.

Figure 4A:
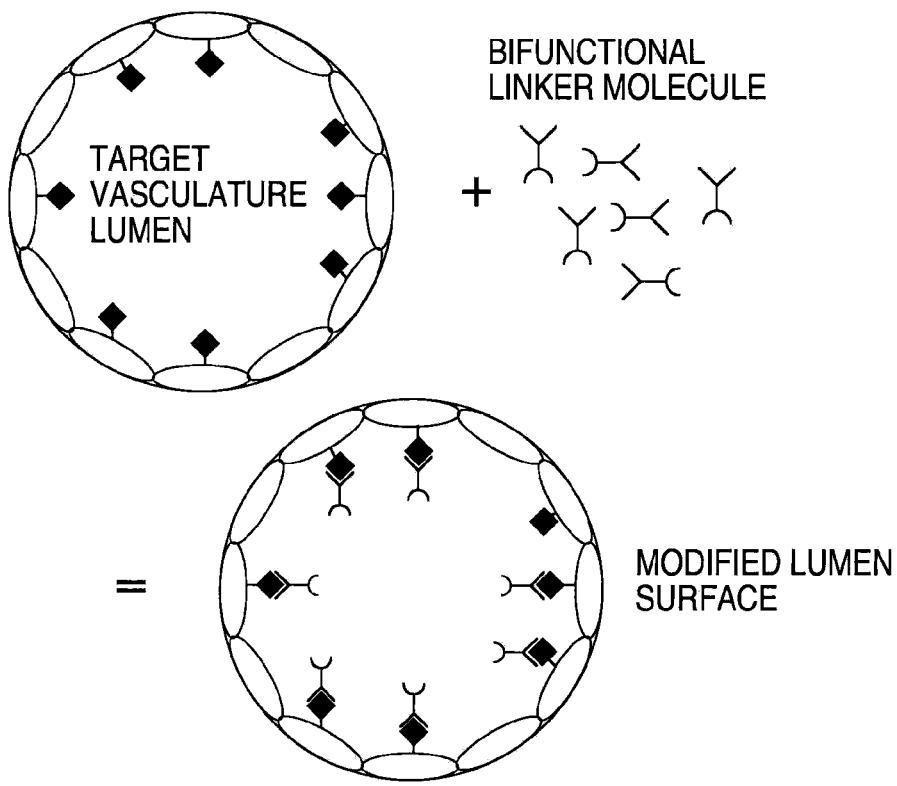
FIG. 4A illustrates surface modified endothelial cells.
Figure 4B:
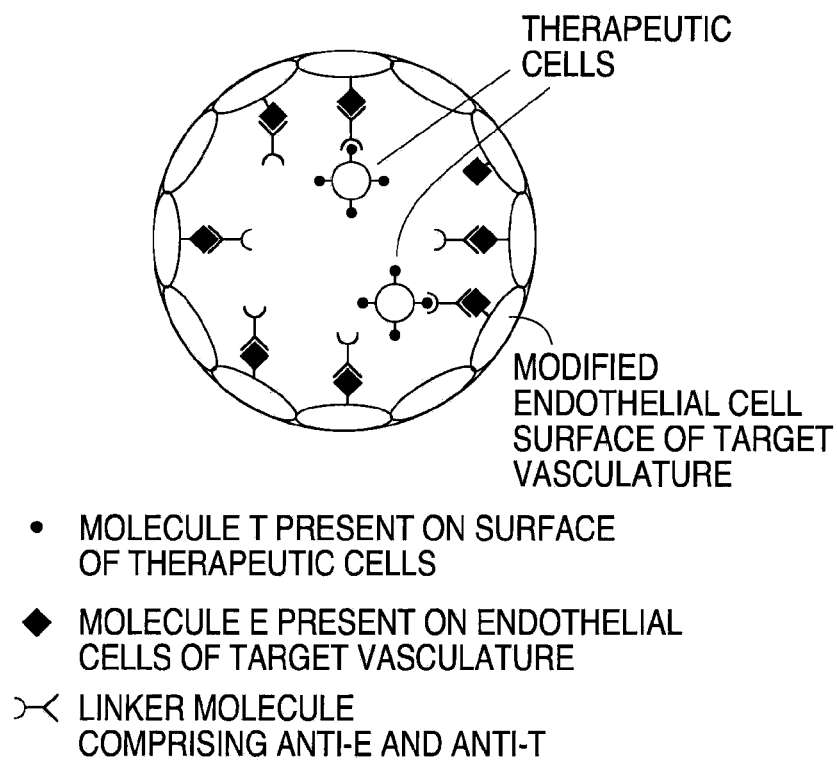
FIG. 4B illustrates therapeutic cells attached to a lumen surface by bi-functional linker molecules.

In another embodiment, bi- or multifunctional linker molecules are infused/injected into the target area vasculature prior to, or simultaneously with, the infusion of therapeutic cells, where at least one functionality of the linker molecule has affinity to the surface of the lumen surface of the target area vasculature, e.g., endothelial cell surface, and at least one other functionality has affinity to the surface of the therapeutic cells, as illustrated in FIGS. 4A and 4B. FIG. 4A illustrates endothelial cells having a surface modified with bi-functional linker molecules. FIG. 4B illustrates therapeutic cells attached to a lumen surface by bi-functional linker molecules. To enhance accessibility, the functionalities may be separated by a spacer, such as a hydrophilic polymer chain, e.g., PEG. For multifunctional linkers, the spacer may have branches or be of star form.

For example, a CD133-antibody linked via a PEG spacer to a CD31-antibody is used to modify the surface of an endothelial cell resident at the lumen surface of the target vasculature. The CD31 antibody has affinity to the CD31 receptor present at the surface of the endothelial cells, while the CD133 antibody has affinity to the CD133 molecule on the surface of the therapeutic cell, e.g., a therapeutic stem cell. To modify the surface of the endothelial cell, the bifunctional antiCD133-PEG-antiCD31 compound is infused into the target vasculature. As the antiCD31 moiety attaches to the CD31 receptor, the endothelial cell surface will effectively present anti-CD133 antibodies with affinity to the surface of an endothelial cell found in the target vasculature.

Alternatively, a homo-bifunctional linker molecule is used. For example, two anti-CD34 antibodies are joined by a short carbon linker and are used to modify the surface of resident endothelial cells of microvasculature. While one of the two antibody moieties adheres to CD34 present on the surface of capillary endothelial cells, the other anti-CD34 moiety is presented outward. Therapeutic cells having CD34 on their surface bind to endothelium pretreated in this fashion.

Figure 5A:
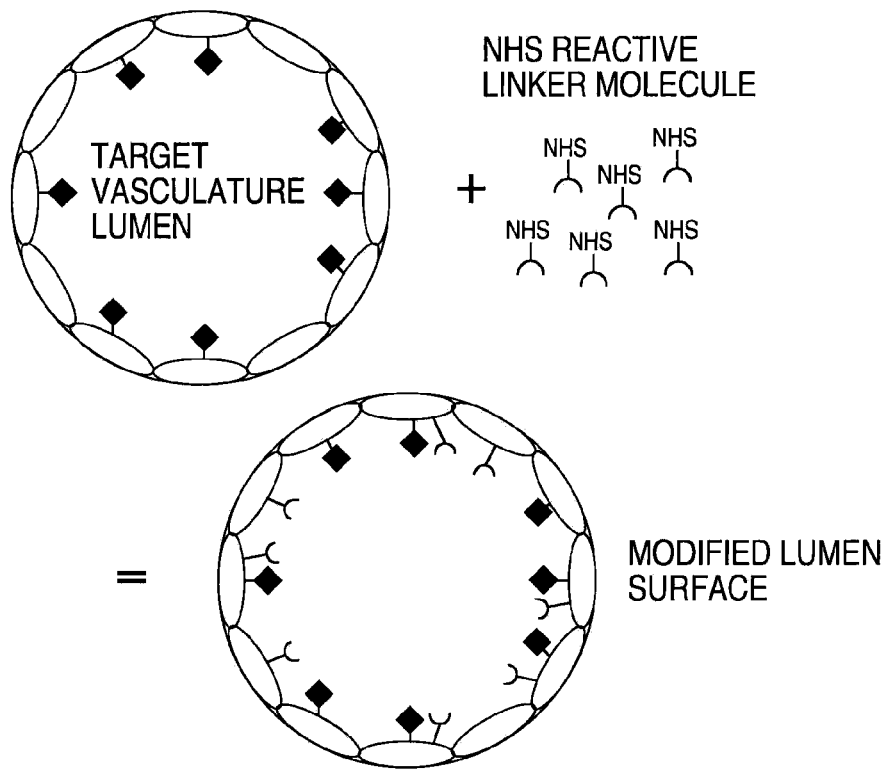
FIG. 5A illustrates endothelial cells attached to NHS reactive linker molecules.
Figure 5B:
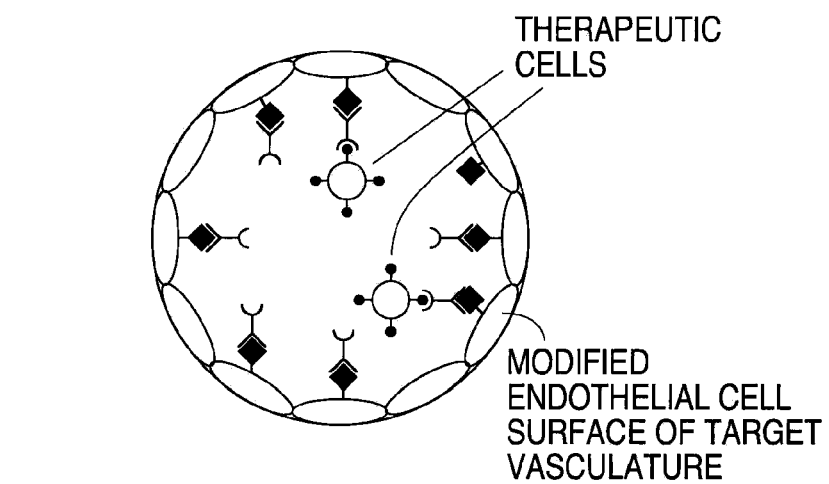
FIG. 5B illustrates therapeutic cells attached to a lumen surface by NHS reactive linker molecules.

In another embodiment, molecules or molecular moieties possessing affinity to the surface of the therapeutic cells may be chemically conjugated to the luminal surface of the target area vasculature, as illustrated in FIGS. 5A and 5B. FIG. 5A illustrates surface modification of lumen cells using NHS reactive linker molecules. In the figure, the NHS linker molecules each include NHS and anti-T. FIG. 5B illustrates a therapeutic cell attached to an endothelial cell of the target vasculature. A molecule or molecular moiety is conjugated to the lumen surface via a spacer molecule to enhance accessibility. A molecule may possess more than one molecular moiety with affinity to the target surface, in which case the spacer may be branched. Chemical conjugation is achieved by infusion of said molecules into the target area vasculature. To enhance the efficiency of the conjugation, the target area vasculature is flushed with saline prior to infusion of attachment molecules. Attachment molecules may be chemically conjugated, i) to amine groups using reactive esters, epoxide, ii) to sulfhydryl groups using maleimides, vinyl sulfones, or iii) to carboxyl groups using dimethylaminopropyl-carbodiimide (EDC) chemistry.

For example, the lumen surface of the target vasculature (e.g. capillary endothelial cells) may be modified by antibodies to receptors present on the surface of the therapeutic, e.g., stem cells (e.g. CD34, CD133, KDR). This may be done by infusing a VS-PEG-antibody molecule into the target vasculature and thereby, conjugating the antibody to sulfhydril groups present on the surface of endothelial cells of the target vasculature. A VS-PEG-antibody molecular construct may be made as described above.

In additional embodiments, other antibodies, fragments thereof, or molecules other than antibodies may be conjugated to the lumen surface of the target vasculature.

Molecules or molecular moieties possessing affinity to the surface of the therapeutic cells may be introduced and anchored in the membrane of endothelial cells of the target area vasculature by liposomal or micelle delivery.

For example, CD31 antibodies or fragments thereof may be conjugated to a phosphatidyl ethanolamine lipid with di-C16 or longer chains. These lipid-antibody conjugated may be embedded in micelles or liposomes and infused into the target area. Alternatively, hydrophobic peptide alpha-helices (such as poly-leucine) may serve as membrane anchors.

Circulating endothelial progenitor cells amass at sites of injury (Asahara et al., *Science,* 275:964-966 (1997); Asahara et al., *Circulation Research,* 85: 221-228 (1999)). Sites of injury are characterized by local cell irritation. The infusion of mild irritants, such as slightly acidic or basic buffers, diluted ethanol, and lactic acid, prior to infusion of the therapeutic cells to the target area may therefore increase cell retention. In one embodiment, an agent such as but not limited to ethanol (diluted to 0.01-0.5% by volume); an acidic buffer (i.e., a buffer having a pH in the range of about 5.5 to about 7.0, e.g., pH 6.5±0.5; a basic buffer (i.e. a buffer having a pH in the range of about pH 8.0 to about pH 9.0, e.g., pH 8.0-8.5; high concentration saline (i.e., a saline solution in the range of about 180 mM to about 300 mM NaCl, e.g., about 200-250 mM NaCl); a heated solution, e.g. a saline solution in the range of about 38-42° C., e.g., about 39-40° C.

In another embodiment, the infusion of stimulants, such as cytokines, chemokines, growth factors, hormones, nitric oxide (NO) and other messenger molecules prior to infusion of the therapeutic cells to the target area may increase cell retention.

IV. Induction of Transient, Localized Ischemia

In certain embodiments, the subject matter includes devices and methods that provides a means of delivering therapeutic cells, e.g., previously prepared cells, to a target site, such as the heart, and promoting the engraftment, e.g., absorption, of the cells into the target area, e.g., into the myocardium. The cells may be intended to produce any number of different effects. One example is to promote myocardial regeneration following an infarct by causing therapeutic cells to be absorbed by the heart.

Current methods focus on initially establishing ischemic conditions in order to activate receptors that promote call absorption. This is accomplished by inflating an occlusion balloon within the coronary vasculature. The balloon is later deflated and cells are then injected into the coronary arteries. The cells travel down stream to the ischemic region to be absorbed. This method is undesirable in several respects. First, the necessary vessel occlusion introduces a level of patient risk while at the same time making the patient extremely uncomfortable. Second, once the therapeutic cells are introduced, they readily flow past the ischemic region such that the opportunity for absorption is minimal. The concepts presented herein are intended to address these concerns. Each provides a "controlled" method of introducing ischemia while increasing the "soak time" such that the opportunity for cell absorption is also increased.

Herein a device is described to inject medical grade carbon dioxide ($CO_2$) into the desired artery. $CO_2$ is an established alternate angiographic contrast agent, and can be delivered by pump or injection (see Cronin et al., *Clin. Radiol.*, 60: 123-125 (2005)). Rather than delivering a bolus of $CO_2$, the device described herein delivers the gas continuously in the form of a stream of small bubbles. The $CO_2$ bubbles induce a localized, hypoxic environment in the arterial and/or venial system. By "small bubbles" or "microbubbles" is meant a bubble that can pass through a capillary, for example, a $CO_2$ bubble having a diameter of less than about 6 microns (typically about 3 microns-about 6 microns). In one embodiment, $CO_2$ microbubbles of the size of ultrasound contrast media can be used. In addition, microbubbles larger than 6 microns can be used to occlude microvessels temporarily until the microbubble disintegrates and blood flow resumes, which occlusion will create an ischemic environment due to the occlusion of flow and due to elevated carbon dioxide generated by the bubble. The lack of flow will also facilitate therapeutic cell adhesion in the vicinity of the ischemic environment.

If necessary, these bubbles may be small enough and plentiful enough to create a dispersion between the flowing blood and the $CO_2$. The $CO_2$ bubbles displace the blood such that ischemia is introduced, however, the artery remains patent such that blood continues to flow.

The bubble infusion rate is adjusted as a means of regulating the level of ischemia (e.g., by active regulation of by use of a predetermined, fixed setting). A steady-state level of ischemia is established that produces the necessary preconditioning (receptor activation) at the target site. The time required to absorb the $CO_2$ will result in an overall reduced flow rate of the blood/$CO_2$ combination. Thus a reduced level of perfusion is also established.

In one embodiment, previously prepared therapeutic cells (stem cells, for example) are injected alongside the $CO_2$ via the same catheter such that the blood/$CO_2$ mixture now becomes a mixture of blood, $CO_2$, and cells. Because some reduced level of perfusion remains present, the cells are slowly carried down stream and enter the ischemic capillary region. They slowly pass across this region and are absorbed by receptors activated by the ischemic condition.

The $CO_2$ component maintains the required ischemic level to promote cell absorption. The reduced flow rate provides additional time for the stem cells to be absorbed as they pass across the ischemic region.

Thus, in one embodiment a method entails a continuous process rather than a repetitive series of vessel occlusions followed by stem cell injections. In addition, a myocardial infarct site can be readily targeted by advancing the device more distally than a device that includes the use of a balloon.

Figure 6A:
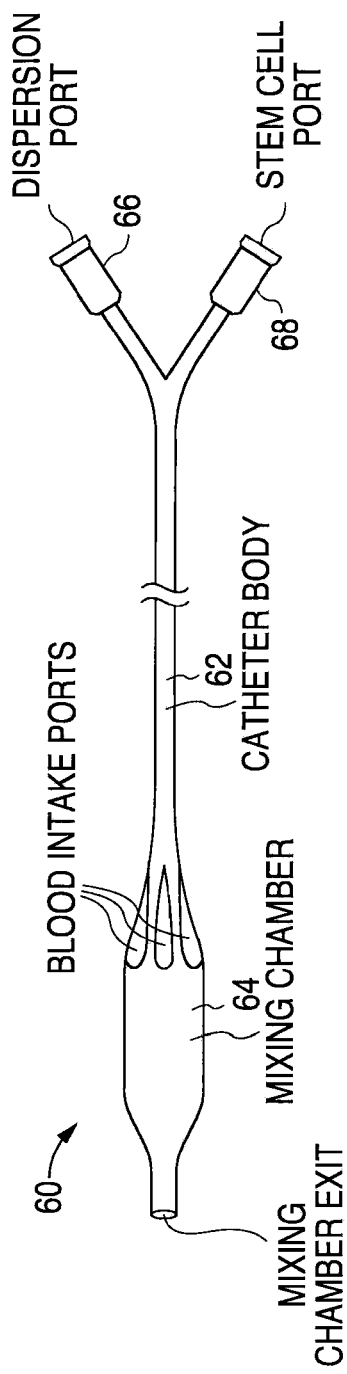
FIG. 6A illustrates a system having a dual lumen catheter body and a bubble producing mixing chamber.
Figure 6B:
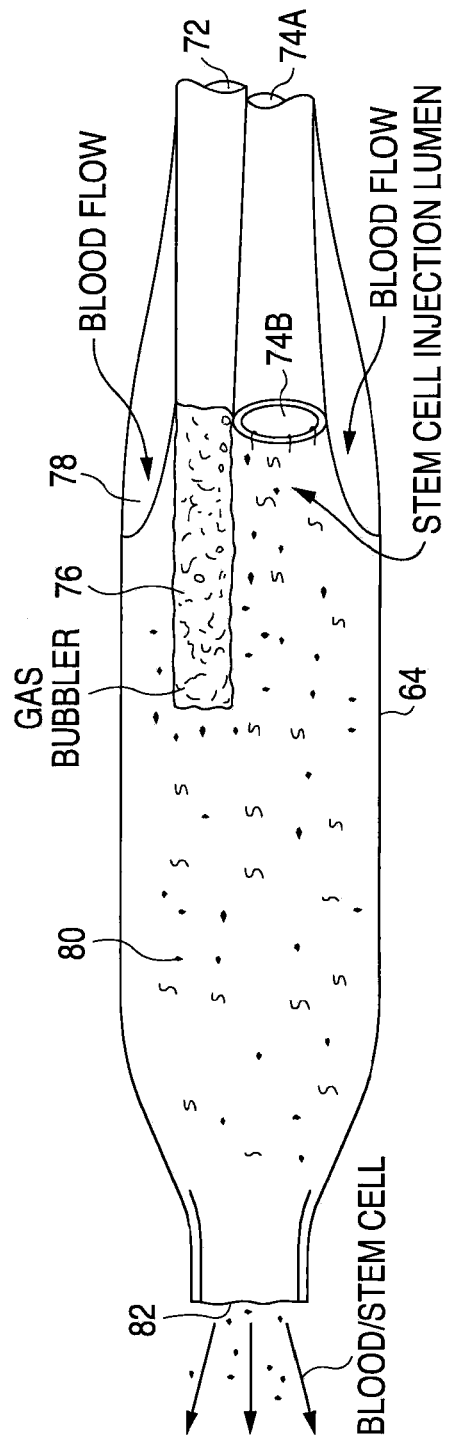
FIG. 6B illustrates a bubble producing mixing chamber.

In an alternative embodiment, the "dispersion" is created by passing the $CO_2$ through a small sponge contained within the distal tip of the catheter, as illustrated in FIG. 6B.

In one embodiment, saline is used to introduce ischemia.

In one example, therapeutic cells and $CO_2$ microbubbles are delivered to a target site via a catheter. The $CO_2$ microbubbles burst and deliver $CO_2$ to a localized target area, which preconditions the target site to enhance the engraftment of the therapeutic cells.

In one example, the $CO_2$ microbubbles are delivered in a continuous stream by using a porous element of a catheter head. The porous element, in one example, includes a sponge-type material or a porous ceramic or synthetic material.

FIG. 6A illustrates exemplary catheter system 60 having implantable mixing chamber 64 at a distal end of catheter body 62 and dispersion port 66 and therapeutic cell port 68 at a proximate end. Catheter body 62, in the example illustrated includes two lumens. Dispersion port 66 is configured to receive gaseous $CO_2$ and therapeutic cell port 68 is configured to receive therapeutic cells. Port 66 and port 68, in various examples, are coupled to a pump or syringe.

FIG. 6B illustrates bubble producing mixing chamber 64 receives a dispersion via line 72 and therapeutic cells via line 74A. Line 72 is coupled to dispersion port 66 and terminates within reservoir 80 at bubbler 76. Bubbler 76, in the example illustrated, includes a sponge material, however other bubble producing materials can also be used. Line 74A is coupled to therapeutic cell port 68 and terminates within reservoir 80 at end 74B. End 74B, in the figure, is a plain end and releases stem cells denoted herein by the symbol "s." Blood enters reservoir 80 at entry port 78. Blood entering reservoir 80 mixes with the bubbles formed by bubbler 76 and therapeutic cell(s) from end 74B and exits mixing chamber 64 at discharge port 82 in the form of a dispersion.

In one example, the $CO_2$ bubbles occlude the capillary flow.

In one example, ischemia is induced using a catheter to inject $CO_2$ in a stream of tiny bubbles. In one example, medical grade $CO_2$ is injected into an artery in a stream of tiny bubbles having a foam-like consistency. The bubbles in the foam are sufficiently small to approximate an dispersion of blood and $CO_2$. The concentration of $CO_2$ required to induce ischemia can be calculated based on the concentration of oxygen required in the region. A pump or valve can be used to control the perfusion, or flow rate, of solution into the vasculature.

According to one theory, the time required to absorb the $CO_2$ will effectively reduce the flow rate of the blood and $CO_2$ combination. As such, a reduced level of profusion is established. Reduced level of profusion is established since the $CO_2$ displaces the blood flow and the therapeutic cells that are being introduced.

According to one theory, $CO_2$ micro bubbles and therapeutic cells increase Brownian motion, thus increasing the opportunity for cells to bump against the surface of the vessel wall. In one example, the $CO_2$ micro bubbles and therapeutic cells forms an dispersion that is delivered in a single continuous process.

In one example, the target endothelium is preconditioned by introducing the $CO_2$ followed by a bolus of therapeutic cells. The flow rate can be modulated to achieve a desired engraftment. In one example, the rate of blood flow is controlled and maintained at a non-zero level to induce a regional ischemic event.

A. Microsphere Induced Occlusion

In one embodiment, a device is placed proximal to the target infusion tissue. A controlled release of microsphere materials are released into the vessel. These spheres are delivered to the capillary bed and occlude or "plug up" the capillary bed. By plugging up or occluding some of the capillaries, the amount of oxygen delivered is reduced and ischemia is thereby created. Thus, an appropriate delay is elapsed, such as the time in which blood in the target tissue is displaced, to induce controlled ischemic conditions. In one embodiment, microspheres of 9-15 micron diameter may be used to occlude capillaries. The microspheres occlusion may be such that all flow is blocked in the capillary. In this case, lesser amounts of oxygen may be delivered by adjacent unoccluded capillaries, thereby creating an ischemic environment. In another embodiment, the microspheres may block the capillary in such a way that red blood cells cannot pass through and deliver large amounts of oxygen, but blood plasma can pass through to deliver very small amounts of oxygen, again creating an ischemic environment. In one embodiment, microspheres may reduce oxygen delivery by 50 to 75%. In another embodiment, the microspheres may reduce oxygen delivery by 60-95%. In another embodiment, the microspheres may be composed of a biodegradable or bioabsorbable material that would limit the duration of the occlusion to a few days. Therapeutic cells are then introduced into the target tissue and allowed to "soak" for an appropriate period of time. The spheres are then deactivated, and normal blood flow resumes to the tissue.

In one embodiment, this process is controlled by a blocking balloon on the delivery device.

In another embodiment, this process is computer controlled with automatic timing, injections, and monitoring of EKG for proper and dangerous ischemic conditions.

In one embodiment, the microspheres are dissolvable and in one example, are made of bioabsorbable material that is absorbed at different periods of time. Examples of bio-absorbable materials include, but is not limited to, degradable polymers such as polycaprolactone, PLGA poly(lactide-co-glycolide), Polyester-amide, polyphosphazine, tyrosine carbonate, etc., or Alginate crosslinked with divalent Ca, Ba or Sr cations. The microspheres may also be made of an extracellular matrix protein such as collagen or gelatin, crosslinked with glutaraldehyde to prevent quick dissolution.

The microspheres occlude the target site and are later dissolved upon application of energy or after a period of time. For example, by applying thermal energy, a solvent, ultrasonic energy or radio frequency energy, the microspheres dissolve. In one example, the microspheres dissolve upon exposure to a particular temperature.

In one example, the fluid flow is temporarily occluded after infusion of therapeutic cells. In one example, shear forces are exerted on both the endothelial cells and the therapeutic cells based on the relative movement there between. Accordingly, as the flow rate increases, the shearing forces increase. To reduce the flow rate, a flow resistor is placed in the lumen of the vasculature. The flow resistor is positioned upstream relative to the target site, however, in one example, the flow resistor is positioned downstream.

In one example, the flow rate is controlled by retro-profuse cells at the target site. Retro-profusion entails a distal occlusion which reverses the fluid flow. The reversed fluid flow occurs as a result of pressure applied to drive the cells up the vascular bed rather than downstream.

In various examples, therapeutic cells are delivered through a catheter. The target vessel is occluded for a brief time period (three minutes in one example) to induce ischemia at the target site. Following occlusion, therapeutic cells are delivered.

In one example, the fluid flow is temporarily stopped and then immediately thereafter therapeutic cells are infused. In one example, the vessel is occluded after the time of infusion such that an effective number of the infused therapeutic cells are located at the target site when the flow is at a reduced rate. The target area is a short distance from the infusion site. In one example, the occlusion is established between approximately 0.5 and 2 seconds after infusion. Times greater or less than 0.5 and 2 seconds are also contemplated. In one example, a majority of therapeutic cells are at the target site when the occlusion occurs.

The therapeutic cells will be spatially distributed in the vessel soon after the time of infusion. The delay between therapeutic cell infusion and vessel occlusion is selected to provide that the bulk of therapeutic cells are in the target region at the time of vessel occlusion.

In one example, therapeutic cells are infused in a sequence of pulses during which the flow rate in the vessel is varied between fully occluded and no resistance. In such an example, the therapeutic cells arrive in multiple groups and the occlusion occurs in a time sequence such that each group briefly pauses for a period of time as it travels through the target area. In one example, an estimate of the flow rate informs the decision as to when the therapeutic cells are injected as a function of the location of the infusion site relative to the target site and when the vessel is occluded. A typical flow rate for a healthy heart is approximately 40 ml per minute which will vary with vessel size and location. In one example, the flow rate is measured using a sensor or imaging of the vasculature.

Various catheter designs can be used to introduce an ischemia producing agent, such as $CO_2$. FIGS. 6A and 6B illustrate one such example tailored to generate small $CO_2$ bubbles by forcing pressurized $CO_2$ across a membrane. The membrane is selected to have a micro porosity to form extremely small bubbles that float into capillary beds and momentarily plug the capillary beds to cause ischemia.

In one method, an artery flowing into the target area for delivery of therapeutic cells is momentarily plugged for some predetermined amount of time using $CO_2$, which causes more ischemia, which is then followed with therapeutic cell delivery.

In various example, the capillary bed is plugged or occluded either partially or wholly to fluid flow. The capillary bed can be occluded using a flow resistor as described elsewhere in this document.

According to one theory, the $CO_2$ dispersion flowing through the vasculature is absorbed in a gas exchange in the lungs due to vapor pressures.

In one example, the level of ischemia in a target location is monitored using a sensor. The sensor output is used in a feedback loop to control the level of ischemia. The level of ischemia can be regulated by adjusting the resistance of an element or by changing a concentration of $CO_2$ or applied pressure. In one example, the feedback signal is generated using an oxygen sensor positioned on the back side of the capillary bed in a vein.

According to one theory, introduction of a $CO_2$ dispersion is effective to create increased Brownian motion. Brownian motion refers to the random movement of microscopic particles suspended in liquids or gasses resulting from the impact of molecules of the fluid surrounding the particle. Brownian motion causes increased "bumping," which refers to the manner in which the therapeutic cells travel along the endothelial target area, thus increasing the likelihood of bonding with an adhesion molecule.

A catheter having a sponge and a mixing chamber is illustrated in FIGS. 6A and 6B. The catheter includes multiple lumens and in the example illustrated, one lumen is used to inject $CO_2$ and the other lumen is used to inject the therapeutic cells into the catheter. The first lumen terminates in a sponge that serves to generate micro bubbles. The mixing chamber receives the therapeutic cells, blood and the $CO_2$, thus forming a dispersion.

Other examples are also contemplated, including, for example, a catheter having multiple lumens in which the $CO_2$, the therapeutic cells and blood are combined. The $CO_2$, in various examples, would be in the form of micro bubbles. A vent is provided to allow blood to fill into the mixing reservoir. Other methods and structures are also contemplated for enhancing mixing in the chamber before delivery to the vasculature.

According to one example, the $CO_2$ is injected and mixed with blood and travels downstream to the target area. The $CO_2$ causes ischemia of the vessel. In one example, the $CO_2$ is introduced in a series of small injections interspersed by delay periods.

Other delivery regimens are also contemplated. For example, after a period of time during which the $CO_2$ is absorbed and the blood flow resumes, another bolus of $CO_2$ is introduced along with therapeutic cells. The dwell time of the therapeutic cells can be controlled by the $CO_2$ delivery regimen. In one example, a thickener, gel or other agent is added in the mixing chamber of the catheter to increase the viscosity. An exemplary thickener includes $CO_2$ foam, micro spheres or liposomes.

In one example, micro spheres include small spheres of a flow occluding substance that can later be dissolved or dispersed. For example, micro spheres fabricated of albumin (e.g., Optison) will disperse or dissolve when subjected to an externally applied field of ultrasonic energy or radio frequency energy. As another example, micro spheres fabricated of poly(lactide-co-glycolide) (PLGA) will biodissolve after a period of time.

According to one theory, the micro spheres occlude or plug the capillary bed since their dimensions are physically too large to pass through the bed.

To form the $CO_2$ bubbles, $CO_2$ is forced over a porous membrane or the sponge. FIG. 6B illustrates gas bubbler 76 fabricated of a sponge material disposed within a reservoir of a mixing chamber. Other configurations are also contemplated, including a dual reservoir mixing chamber. In such an example, one reservoir receives $CO_2$ and the other reservoir receives the therapeutic cells. The $CO_2$ reservoir includes a porous medium through which bubbles are formed. One lumen is ported to the chamber. Another port allows blood from the artery to bypass or flow into the chamber.

In operation, the catheter perfuses $CO_2$, blood and therapeutic cells. In one example, a lumen of a catheter is terminated with a porous medium through which stem cells, blood and carbon dioxide bubbles perfuse. In one example, blood enters through a bypass port and therapeutic cells are injected into a chamber concurrent with $CO_2$ bubbling and the mixture is discharged from the chamber at the distal end of the catheter. In addition to blood, $CO_2$ and therapeutic cells, other materials can be delivered using the catheter of the present subject matter. For example, a drug or other agent to cause ischemia or otherwise improve engraftment can be delivered using the present catheter either with or without the porous medium. The drug or other agent can be a gaseous, solid or liquid substance.

V. Alternative Examples

In addition to the examples presented above, other embodiments are also contemplated.

In an alternative embodiment, a "therapeutic cell" includes a therapeutic drug carrier such as a liposome or a polymer particle with a surface molecule that has an affinity to the lumen surface of the vasculature.

In one example, the present subject matter entails surface recognition through surface tailoring. For example, surface tailoring of the both the therapeutic cell and the target cell is employed to enhance engraftment. The surface modification methods presented elsewhere in this document can be combined synergistically such that, for example, the therapeutic cell surfaces are modified to present molecular moiety A (for example, through genetic modification, surface modification or other methods) and the lumen surface of the target vasculature area (endothelial cells) are modified to present molecular moiety B where moiety A has affinity to moiety B. Moiety A does not necessarily have an affinity to endothelial surface and moiety B does not necessarily have an affinity to the surface of the therapeutic cells). For one example, avidin is conjugated to one surface and biotin is conjugated to the complementary surface. Biotin may be conjugated to lysines of membrane proteins present at the cellular surface using NHS-PEG-biotin molecules. Avidin may be bound to the biotin present on the cell surface using an additional incubation in avidin, effectively immobilizing avidin at the cell's surface.

All patents and publications referenced or mentioned herein are indicative of the levels of skill of those skilled in the art to which the subject matter pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. A catheter comprising:
   a catheter body;
   a mixing chamber attached to a distal end of the catheter body, the mixing chamber having an outlet;
   a first lumen within the catheter body, the first lumen configured to convey gas to the mixing chamber;
   a porous material coupled to the first lumen to generate m bubbles within the mixing chamber;
   a second lumen within the catheter body, the second lumen configured to convey a cell to the mixing chamber; and
   a bypass port configured to admit blood into the mixing chamber.

2. The catheter of claim 1, further including a pump coupled to a dispersion port, the dispersion port coupled to a proximal end of the first lumen.

3. The catheter of claim 1, further including a pump coupled to a cell port, the cell port coupled to a proximal end of the second lumen.

4. The catheter of claim 1, wherein the porous material includes a sponge.

5. The catheter of claim 1, wherein an outer wall of the mixing chamber is located beyond the distal end of the catheter body.

6. The catheter of claim 5, wherein the outer wall contains a reservoir of the mixing chamber, the reservoir is located beyond the distal end of the catheter body, and the reservoir is configured to receive gas bubbles generated by the porous material and to receive the cell conveyed by the second lumen.

7. The catheter of claim 6, wherein the first lumen terminates within the reservoir.

8. The catheter of claim 6, wherein the second lumen terminates within the reservoir.

9. The catheter of claim 6, wherein the first lumen and the second lumen terminate within the reservoir.

10. The catheter of claim 6, wherein an outlet of the second lumen opens directly to the reservoir.

11. The catheter of claim 5, wherein the outlet of the mixing chamber is formed through the outer wall of the mixing chamber, and the outlet is configured to discharge the gas bubbles generated by the porous material and to discharge the cell conveyed by the second lumen.

12. The catheter of claim 5, wherein the bypass port is formed though the outer wall of the mixing chamber.

13. The catheter of claim 5, wherein the porous material is disposed within the outer wall of the mixing chamber.

14. The catheter of claim 13, wherein the first lumen terminates at the porous material disposed within the outer wall of the mixing chamber.

15. The catheter of claim 1, wherein the first lumen includes a first inlet and a first outlet, the first outlet configured to deliver gas to the mixing chamber.

16. The catheter of claim 1, further comprising a dispersion port at a proximal end of the catheter body, the dispersion port configured to receive the gas to be conveyed by the first lumen, the proximal end of the catheter body located opposite the distal end of the catheter body.

17. The catheter of claim 1, wherein the first lumen terminates at the porous material.

18. The catheter of claim 1, wherein an outlet of the second lumen opens directly to the mixing chamber.

* * * * *